(12) United States Patent
Chen et al.

(10) Patent No.: US 12,240,901 B2
(45) Date of Patent: Mar. 4, 2025

(54) HUMANIZED ANTI-BASIGIN ANTIBODIES AND THE USE THEREOF

(71) Applicant: FOURTH MILITARY MEDICAL UNIVERSITY, Shaanxi (CN)

(72) Inventors: Zhinan Chen, Shaanxi (CN); Ping Zhu, Shaanxi (CN); Wan Huang, Shaanxi (CN); Zheng Zhang, Shaanxi (CN); Yang Zhang, Shaanxi (CN); Mengyao Zhang, Shaanxi (CN); Huijie Bian, Shaanxi (CN); Jianli Jiang, Shaanxi (CN)

(73) Assignee: FOURTH MILITARY MEDICAL UNIVERSITY, Xi'an (CN)

(*) Notice: Subject to any disclaimer, the term of this patent is extended or adjusted under 35 U.S.C. 154(b) by 1090 days.

(21) Appl. No.: 16/097,274

(22) PCT Filed: May 2, 2017

(86) PCT No.: PCT/CN2017/082713
§ 371 (c)(1),
(2) Date: Oct. 29, 2018

(87) PCT Pub. No.: WO2017/186182
PCT Pub. Date: Nov. 2, 2017

(65) Prior Publication Data
US 2019/0270809 A1 Sep. 5, 2019

(30) Foreign Application Priority Data
Apr. 29, 2016 (CN) .......................... 201610285139.4

(51) Int. Cl.
| | | |
|---|---|---|
| C07K 16/30 | (2006.01) | |
| A61K 9/00 | (2006.01) | |
| A61K 39/395 | (2006.01) | |
| A61P 33/06 | (2006.01) | |
| A61P 35/00 | (2006.01) | |
| C07K 16/00 | (2006.01) | |
| C07K 16/28 | (2006.01) | |
| C07K 16/32 | (2006.01) | |
| C07K 16/42 | (2006.01) | |

(52) U.S. Cl.
CPC ........ *C07K 16/2803* (2013.01); *A61K 9/0019* (2013.01); *A61K 39/395* (2013.01); *A61P 33/06* (2018.01); *A61P 35/00* (2018.01); *C07K 16/005* (2013.01); *C07K 16/32* (2013.01); *C07K 16/42* (2013.01); *C07K 2317/24* (2013.01); *C07K 2317/622* (2013.01); *C07K 2317/92* (2013.01)

(58) Field of Classification Search
CPC .................. A61K 39/39558; A61K 39/39541
See application file for complete search history.

(56) References Cited

U.S. PATENT DOCUMENTS

| | | | | |
|---|---|---|---|---|
| 2001/0021516 A1* | 9/2001 | Wei | .................. | A61P 37/06 435/69.1 |
| 2003/0017534 A1* | 1/2003 | Buelow | .................. | A61P 35/00 435/69.1 |
| 2005/0214302 A1* | 9/2005 | Nakada | .............. | C07K 16/2896 424/155.1 |

FOREIGN PATENT DOCUMENTS

| | | |
|---|---|---|
| AU | 2015213308 A1 | 9/2015 |
| CN | 101054416 A | 10/2007 |
| CN | 101550416 A | 10/2009 |
| CN | 104086654 A | 10/2014 |
| CN | 105820250 A | 8/2016 |
| JP | 2013509879 A | 3/2013 |
| WO | WO2018/165619 * | 9/2018 |

OTHER PUBLICATIONS

Bendig M. M. (Methods: A Companion to Methods in Enzymology, 1995; 8:83-93) (Year: 1995).*
Rudikoff et al. (Proceedings of the National Academy of Sciences USA, vol. 79, p. 1979-1983, 1982) (Year: 1982).*
Panka et Al. (Proceedings of the National Academy of Sciences USA, vol. 85, p. 3080-3084, 1988) (Year: 1988).*
Portolano (The Journal of Immunology, vol. 150, No. 3, p. 880-887, 1993) (Year: 1993).*
Paul (Fundamental Immunology, 3rd Edition, 1993, pp. 292-295) (Year: 1993).*
Evans et Al. (Q. J. Med 1999: 92: 299-307) (Year: 1999).*
Schiffman et Al. (The New England Journal of Medicine, Vo. 353, No. 20, p. 2101-2104, 2005) (Year: 2005).*
Cuzick et Al. (The Lancet, vol. 361, p. 296-300, 2003) (Year: 2003).*

(Continued)

*Primary Examiner* — Michael Allen
(74) *Attorney, Agent, or Firm* — Jun He Law Offices P.C; Zhaohui Wang

(57) ABSTRACT

The present disclosure provides a humanized anti-BASIGIN antibody or antigen binding fragment thereof, which comprises heavy chain variable region ($V_H$) comprising an amino acid sequence of SEQ ID NO: 1; optionally further comprise light chain variable region ($V_L$) comprising an amino acid sequence of SEQ ID NO: 2. The present disclosure also provides a composition comprising the humanized anti-BASIGIN antibody or antigen binding fragment thereof, an isolated nucleic acid sequence encoding the humanized anti-BASIGIN antibody or antigen binding fragment thereof, a vector comprising the nucleic acid, a host cell comprising the vector, and use of the humanized anti-BASIGIN antibody or antigen binding fragment thereof.

12 Claims, 5 Drawing Sheets
Specification includes a Sequence Listing.

(56) References Cited

OTHER PUBLICATIONS

Hernandez-Ledesma (Peptides, vol. 30, p. 426-430, 2009) (Year: 2009).*
Kappell et Al., Current Opinions in Biotechnology, vol. 3, p. 548-553, 1992 (Year: 1992).*
Houdebine (Comparative Immunology, Microbiology, and Infectious Diseases, vol. 32, p. 107-121, 2009) (Year: 2009).*
Baxevanis (Expert Opinion: Drug Discovery, vol. 3, No. 4, p. 441-452, 2008) (Year: 2008).*
Komenaka et Al., Clinics in Dermatology, 2004, vol. 22, p. 251-265 (Year: 2004).*
Houdebine et Al., Journal of Biotechnology, vol. 34, p. 269-287, 1994 (Year: 1994).*
Wall et Al., Theriogenology, vol. 45, p. 57-68, 1996 (Year: 1996).*
The extended European Search Report of European Application No. 17788834.4, issued on Sep. 17, 2019.
Examination report No.1 for Australian standard patent application No. 2017255888, issued on Dec. 19, 2019.
Yang, B. "Molecular Modeling and Docking of HAb18G/CD147 with Its Monoclonal Antibody and Antibody Humanization Design." Chinese Master's Theses Full-Text Database (Medicine and Health Sciences)., Apr. 15, 2008 (Apr. 15, 2008), article E059-63.
Zhu, H.B. "Preparation of anti-HAb18G/CD147 antibody fragment (HAb18-huScFv)2-Fc and characterization of in vitro anti-tumor effect." Chinese Master's Theses Full-Text Database (Medicine and Health Sciences)., Dec. 15, 2009 (Dec. 15, 2009), article E059-43.
Ye, H. "Preparation and functional characterization of anti-human monoclonal antibody against recombinant extracellular domain of HAb18G/CD147." Chinese Doctoral Dissertations & Master's Theses Full-Text Database (Master) (Medicine and Health Sciences)., Oct. 15, 2005 (Oct. 15, 2005), article E072-236.
The First Office Action for Japanese Patent Application No. 2018-556501, mailed on Apr. 26, 2021.

* cited by examiner

SEQUENCE LISTING

```
<160> NUMBER OF SEQ ID NOS: 62

<210> SEQ ID NO 1
<211> LENGTH: 116
<212> TYPE: PRT
<213> ORGANISM: Artificial Sequence
<220> FEATURE:
<223> OTHER INFORMATION: Amino acid sequence of humanized heavy chain
      variable region of humanized anti-BASIGIN antibody or antigen
      binding fragment with variations
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid

<400> SEQUENCE: 1
```

```
Glu Val Gln Leu Xaa Glu Ser Gly Gly Gly Leu Val Gln Pro Gly Gly
1               5                   10                  15

Ser Leu Arg Leu Ser Cys Xaa Ala Ser Gly Phe Thr Phe Ser Asn Phe
            20                  25                  30

Trp Met Asn Trp Val Arg Gln Ala Pro Gly Lys Gly Leu Glu Trp Val
            35                  40                  45

Xaa Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Xaa Xaa
65                  70                  75                  80

Leu Tyr Leu Gln Met Asn Ser Leu Xaa Thr Glu Asp Thr Xaa Val Tyr
                85                  90                  95

Tyr Cys Thr Ser Tyr Asp Tyr Glu Tyr Trp Gly Gln Gly Thr Leu Val
            100                 105                 110

Thr Val Ser Ala
        115

<210> SEQ ID NO 2
<211> LENGTH: 107
<212> TYPE: PRT
<213> ORGANISM: Artificial Sequence
<220> FEATURE:
<223> OTHER INFORMATION: Amino acid sequence of humanized light chain
      variable region of humanized anti-BASIGIN antibody or antigen
      binding fragment with variations
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid

<400> SEQUENCE: 2

Asp Ile Gln Met Thr Gln Ser Pro Xaa Xaa Leu Ser Xaa Ser Val Gly
1               5                   10                  15

Asp Arg Val Thr Xaa Xaa Cys Lys Ala Ser Glu Asn Val Gly Thr Tyr
            20                  25                  30

Val Ser Trp Tyr Gln Gln Lys Pro Gly Xaa Xaa Pro Lys Leu Leu Ile
            35                  40                  45

Tyr Gly Ala Ser Asn Arg Tyr Thr Gly Val Pro Xaa Arg Phe Thr Gly
```

```
                  50                  55                  60
Xaa Gly Ser Gly Thr Asp Phe Thr Leu Thr Ile Ser Ser Leu Gln Xaa
 65                  70                  75                  80

Xaa Asp Xaa Ala Thr Tyr Tyr Cys Gly Gln Ser Tyr Ser Tyr Pro Phe
                 85                  90                  95

Thr Phe Gly Ser Gly Thr Lys Leu Glu Ile Lys
            100                 105
```

<210> SEQ ID NO 3
<211> LENGTH: 116
<212> TYPE: PRT
<213> ORGANISM: Artificial Sequence
<220> FEATURE:
<223> OTHER INFORMATION: Amino acid sequence of heavy chain variable
      region (VH) of humanized antibody HP6H8-1

<400> SEQUENCE: 3

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Phe
                 20                  25                  30

Trp Met Asn Trp Val Arg Gln Ala Pro Gly Lys Gly Leu Glu Trp Val
             35                  40                  45

Ser Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Ser Tyr Asp Tyr Glu Tyr Trp Gly Gln Gly Thr Leu Val
            100                 105                 110

Thr Val Ser Ala
        115
```

<210> SEQ ID NO 4
<211> LENGTH: 348
<212> TYPE: DNA
<213> ORGANISM: Artificial Sequence
<220> FEATURE:
<223> OTHER INFORMATION: Nucleic acid sequence of heavy chain variable
      region (VH) of humanized antibody HP6H8-1

<400> SEQUENCE: 4

```
gaagtgcagc ttgtggagtc tggaggaggc ttggtgcaac tggaggatc cctgaggctc      60 tcctgtgccg cctctggatt cactttcagt aacttctgga tgaactgggt ccgccaggct     120
ccagggaagg ggcttgagtg ggtttccgaa attagattga aatctaataa ttatgcaaca     180
cattatgcgg agtctgtgaa agggaggttc accatctcaa gagatgattc caaaaacacc     240
ctgtacctgc agatgaactc cttaaagact gaagacactg ccgtgtatta ctgtaccagc     300
tatgattacg aatactgggg ccaagggact ctggtcactg tctctgca                  348
```

<210> SEQ ID NO 5
<211> LENGTH: 116
<212> TYPE: PRT
<213> ORGANISM: Artificial Sequence
<220> FEATURE:
<223> OTHER INFORMATION: Amino acid sequence of heavy chain variable
      region (VH) of humanized antibody HP6H8-2

<400> SEQUENCE: 5

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Phe
            20                  25                  30

Trp Met Asn Trp Val Arg Gln Ala Pro Gly Lys Gly Leu Glu Trp Val
            35                  40                  45

Ala Glu Ile Arg Leu Lys Ser Asn Asn Tyr Ala Thr His Tyr Ala Glu
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Thr Glu Asp Thr Ala Val Tyr
                85                  90                  95

Tyr Cys Thr Ser Tyr Asp Tyr Glu Tyr Trp Gly Gln Gly Thr Leu Val
            100                 105                 110

Thr Val Ser Ala
        115

<210> SEQ ID NO 6
<211> LENGTH: 348
<212> TYPE: DNA
<213> ORGANISM: Artificial Sequence
<220> FEATURE:
<223> OTHER INFORMATION: Nucleic acid sequence of heavy chain variable
      region (VH) of humanized antibody HP6H8-2

<400> SEQUENCE: 6
gaagtgcagc ttgtggagtc tggaggaggc ttggtgcaac ctggaggatc cctgaagctc      60
tcctgtgccg cctctggatt cactttcagt aacttctgga tgaactgggt ccgccaggct     120
ccagggaagg ggcttgagtg ggttgccgaa attagattga aatctaataa ttatgcaaca     180
cattatgcgg agtctgtgaa agggaggttc accatctcaa gagatgattc caaaaacacc     240
ctgtacctgc aaatgaactc cttaaggact gaagacactg ccgtgtatta ctgtaccagc     300
tatgattacg aatactgggg ccaagggact ctggtcactg tctctgca                  348

<210> SEQ ID NO 7
<211> LENGTH: 116
<212> TYPE: PRT
<213> ORGANISM: Artificial Sequence
<220> FEATURE:
<223> OTHER INFORMATION: Amino acid sequence of heavy chain variable
      region (VH) of humanized antibody HP6H8-3

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Phe
            20                  25                  30

Trp Met Asn Trp Val Arg Gln Ala Pro Gly Lys Gly Leu Glu Trp Val
            35                  40                  45

Ala Glu Ile Arg Leu Lys Ser Asn Asn Tyr Ala Thr His Tyr Ala Glu
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ser Tyr Asp Tyr Glu Tyr Trp Gly Gln Gly Thr Leu Val
            100                 105                 110

<210> SEQ ID NO 8
<211> LENGTH: 348
<212> TYPE: DNA
<213> ORGANISM: Artificial Sequence
<220> FEATURE:
<223> OTHER INFORMATION: Nucleic acid sequence of heavy chain variable
      region (VH) of humanized antibody HP6H8-3

<400> SEQUENCE: 8

```
gaagtgcagc ttgtggagtc tggaggaggc ttggtgcaac ctggaggatc cctgaagctc      60
tcctgtgccg cctctggatt cactttcagt aacttctgga tgaactgggt ccgccaggct     120
ccagggaagg ggcttgagtg ggttgccgaa attagattga atctaataa ttatgcaaca      180 cattatgcgg agtctgtgaa agggaggttc accatctcaa gagatgattc caaaaacacc     240
ctgtacctgc agatgaactc cttaaagact gaagacactg ccgtgtatta ctgtaccagc     300
tatgattacg aatactgggg ccaagggact ctggtcactg tctctgca                  348
```

<210> SEQ ID NO 9
<211> LENGTH: 10
<212> TYPE: PRT
<213> ORGANISM: Mus musculus
<220> FEATURE:
<221> NAME/KEY: DOMAIN
<222> LOCATION: (1)..(10)
<223> OTHER INFORMATION: HCDR1

<400> SEQUENCE: 9

Gly Phe Thr Phe Ser Asn Phe Trp Met Asn
1               5                   10

<210> SEQ ID NO 10
<211> LENGTH: 19
<212> TYPE: PRT
<213> ORGANISM: Mus musculus
<220> FEATURE:
<221> NAME/KEY: DOMAIN
<222> LOCATION: (1)..(19)
<223> OTHER INFORMATION: HCDR2

<400> SEQUENCE: 10

Glu Ile Arg Leu Lys Ser Asn Asn Tyr Ala Thr His Tyr Ala Glu Ser
1               5                   10                  15

Val Lys Gly

<210> SEQ ID NO 11
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: HCDR3

<400> SEQUENCE: 11

Tyr Asp Tyr Glu Tyr
1               5

<210> SEQ ID NO 12
<211> LENGTH: 25
<212> TYPE: PRT
<213> ORGANISM: Homo sapiens

```
<220> FEATURE:
<221> NAME/KEY: DOMAIN
<222> LOCATION: (1)..(25)
<223> OTHER INFORMATION: Human heavy chain FR1
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (23)..(23)
<223> OTHER INFORMATION: Xaa can be any naturally occurring amino acid

<400> SEQUENCE: 12

Glu Val Gln Leu Xaa Glu Ser Gly Gly Gly Leu Val Gln Pro Gly Gly
1               5                   10                  15

Ser Leu Arg Leu Ser Cys Xaa Ala Ser
            20                  25

<210> SEQ ID NO 13
<211> LENGTH: 14
<212> TYPE: PRT
<213> ORGANISM: Homo sapiens
<220> FEATURE:
<221> NAME/KEY: DOMAIN
<222> LOCATION: (1)..(14)
<223> OTHER INFORMATION: Human heavy chain FR2
<220> FEATURE:
<221> NAME/KEY: VARIANT
<222> LOCATION: (14)..(14)
<223> OTHER INFORMATION: Xaa can be any naturally occurring amino acid

<400> SEQUENCE: 13

Trp Val Arg Gln Ala Pro Gly Lys Gly Leu Glu Trp Val Xaa
1               5                   10

<210> SEQ ID NO 14
<211> LENGTH: 32
<212> TYPE: PRT
<213> ORGANISM: Homo sapiens
<220> FEATURE:
<221> NAME/KEY: DOMAIN
<222> LOCATION: (1)..(32)
<223> OTHER INFORMATION: Human heavy chain FR3
<220> FEATURE:
<221> NAME/KEY: VARIANT
<222> LOCATION: (11)..(12)
<223> OTHER INFORMATION: Xaa can be any naturally occurring amino acid
<220> FEATURE:
<221> NAME/KEY: VARIANT
<222> LOCATION: (21)..(21)
<223> OTHER INFORMATION: Xaa can be any naturally occurring amino acid
<220> FEATURE:
<221> NAME/KEY: VARIANT
<222> LOCATION: (26)..(26)
<223> OTHER INFORMATION: Xaa can be any naturally occurring amino acid

<400> SEQUENCE: 14

Arg Phe Thr Ile Ser Arg Asp Asp Ser Lys Xaa Xaa Leu Tyr Leu Gln
1               5                   10                  15

Met Asn Ser Leu Xaa Thr Glu Asp Thr Xaa Val Tyr Tyr Cys Thr Ser
            20                  25                  30

<210> SEQ ID NO 15
<211> LENGTH: 11
<212> TYPE: PRT
<213> ORGANISM: Homo sapiens
<220> FEATURE:
<221> NAME/KEY: DOMAIN
<222> LOCATION: (1)..(11)
<223> OTHER INFORMATION: Human heavy chain FR4
```

<400> SEQUENCE: 15

Trp Gly Gln Gly Thr Leu Val Thr Val Ser Ala
1               5                   10

<210> SEQ ID NO 16
<211> LENGTH: 107
<212> TYPE: PRT
<213> ORGANISM: Artificial Sequence
<220> FEATURE:
<223> OTHER INFORMATION: Amino acid sequence of light chain variable
      region (VL) of humanized antibody HP6H8-1

<400> SEQUENCE: 16

Asp Ile Gln Met Thr Gln Ser Pro Ser Thr Leu Ser Ala Ser Val Gly
1               5                   10                  15

Asp Arg Val Thr Leu Ser Cys Lys Ala Ser Glu Asn Val Gly Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 17
<211> LENGTH: 321
<212> TYPE: DNA
<213> ORGANISM: Artificial Sequence
<220> FEATURE:
<223> OTHER INFORMATION: Nucleic acid sequence of light chain variable
      region (VL) of humanized antibody HP6H8-1

<400> SEQUENCE: 17
gacattcaga tgacccaatc tccctccacc ctgtccgcct cagtgggcga cagggtcacc      60
ctctcctgca aggccagtga gaatgtgggt acttatgtat cctggtatca acagaaacca     120
ggcaaggccc ctaaactgct gatatacggg gcatccaacc ggtacactgg ggtcccctcc     180
cgcttcaccg gcagtggatc tggcacagat ttcactctga ccatcagcag tctgcagccc     240
gaggacttcg caacctatta ctgtggacag agttacagct atccattcac gttcggctcg     300
gggacaaagt tggaaataaa a                                                321

<210> SEQ ID NO 18
<211> LENGTH: 107
<212> TYPE: PRT
<213> ORGANISM: Artificial Sequence
<220> FEATURE:
<223> OTHER INFORMATION: Amino acid sequence of light chain variable
      region (VL) of humanized antibody HP6H8-2

<400> SEQUENCE: 18

Asp Ile Gln Met Thr Gln Ser Pro Ala Ser Leu Ser Ala Ser Val Gly
1               5                   10                  15

Asp Arg Val Thr Ile Ser Cys Lys Ala Ser Glu Asn Val Gly Thr Tyr
            20                  25                  30

Val Ser Trp Tyr Gln Gln Lys Pro Gly Gln Thr Pro Lys Leu Leu Ile

```
            35                  40                  45

Tyr Gly Ala Ser Asn Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gly Gln Ser Tyr Ser Tyr Pro Phe
                85                  90                  95

Thr Phe Gly Ser Gly Thr Lys Leu Glu Ile Lys
            100                 105
```

<210> SEQ ID NO 19
<211> LENGTH: 321
<212> TYPE: DNA
<213> ORGANISM: Artificial Sequence
<220> FEATURE:
<223> OTHER INFORMATION: Nucleic acid sequence of light chain variable
      region (VL) of humanized antibody HP6H8-2

<400> SEQUENCE: 19

```
gacattcaga tgacccaatc tcccgcctcc ctgtccgcct cagtgggcga cagggtcacc      60
atctcctgca aggccagtga gaatgtgggt acttatgtat cctggtatca acagaaacca     120
ggccagaccc ctaaactgct gatatacggg gcatccaacc ggtacactgg ggtcccctcc     180
cgcttctccg gcagtggatc tggcacagat ttcactctga ccatcagcag tctgcagccc     240
gacgacttcg caacctatta ctgtggacag agttacagct atccattcac gttcggctcg     300
gggacaaagt tggaaataaa a                                               321
```

<210> SEQ ID NO 20
<211> LENGTH: 107
<212> TYPE: PRT
<213> ORGANISM: Artificial Sequence
<220> FEATURE:
<223> OTHER INFORMATION: Amino acid sequence of light chain variable
      region (VL) of humanized antibody HP6H8-3

<400> SEQUENCE: 20

```
Asp Ile Gln Met Thr Gln Ser Pro Ser Ser Leu Ser Ala Ser Val Gly
1               5                   10                  15

Asp Arg Val Thr Leu Thr Cys Lys Ala Ser Glu Asn Val Gly Thr Tyr
            20                  25                  30

Val Ser Trp Tyr Gln Gln Lys Pro Gly Gln Ala Pro Lys Leu Leu Ile
        35                  40                  45

Tyr Gly Ala Ser Asn Arg Tyr Thr Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gly Gln Ser Tyr Ser Tyr Pro Phe
                85                  90                  95

Thr Phe Gly Ser Gly Thr Lys Leu Glu Ile Lys
            100                 105
```

<210> SEQ ID NO 21
<211> LENGTH: 321
<212> TYPE: DNA
<213> ORGANISM: Artificial Sequence
<220> FEATURE:
<223> OTHER INFORMATION: Nucleic acid sequence of light chain variable
      region (VL) of humanized antibody HP6H8-3

<400> SEQUENCE: 21

```
gacattcaga tgacccaatc tccctcctcc ctgtccgcct cagtgggcga cagggtcacc    60
ctcacctgca aggccagtga gaatgtgggt acttatgtat cctggtatca acagaaacca   120
ggccaggccc ctaaactgct gatatacggg gcatccaacc ggtacactgg ggtcccctcc   180
cgcttcaccg gcagtggatc tggcacagat ttcactctga ccatcagcag tctgcagccc   240
gacgacttcg caacctatta ctgtggacag agttacagct atccattcac gttcggctcg   300
gggacaaagt tggaaataaa a                                             321
```

```
<210> SEQ ID NO 22
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: LCDR1

<400> SEQUENCE: 22

Lys Ala Ser Glu Asn Val Gly Thr Tyr Val Ser
1               5                   10
```

```
<210> SEQ ID NO 23
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: LCDR2

<400> SEQUENCE: 23

Gly Ala Ser Asn Arg Tyr Thr
1               5
```

```
<210> SEQ ID NO 24
<211> LENGTH: 9
<212> TYPE: PRT
<213> ORGANISM: Mus musculus
<220> FEATURE:
<221> NAME/KEY: DOMAIN
<222> LOCATION: (1)..(9)
<223> OTHER INFORMATION: LCDR3

<400> SEQUENCE: 24

Gly Gln Ser Tyr Ser Tyr Pro Phe Thr
1               5
```

```
<210> SEQ ID NO 25
<211> LENGTH: 23
<212> TYPE: PRT
<213> ORGANISM: Homo sapiens
<220> FEATURE:
<221> NAME/KEY: DOMAIN
<222> LOCATION: (1)..(23)
<223> OTHER INFORMATION: Human light chain FR1
<220> FEATURE:
<221> NAME/KEY: VARIANT
<222> LOCATION: (9)..(10)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa can be any naturally occurring amino acid
<220> FEATURE:
<221> NAME/KEY: VARIANT
<222> LOCATION: (21)..(22)
<223> OTHER INFORMATION: Xaa can be any naturally occurring amino acid
```

```
<400> SEQUENCE: 25

Asp Ile Gln Met Thr Gln Ser Pro Xaa Xaa Leu Ser Xaa Ser Val Gly
1               5                   10                  15

Asp Arg Val Thr Xaa Xaa Cys
            20

<210> SEQ ID NO 26
<211> LENGTH: 15
<212> TYPE: PRT
<213> ORGANISM: Homo sapiens
<220> FEATURE:
<221> NAME/KEY: DOMAIN
<222> LOCATION: (1)..(15)
<223> OTHER INFORMATION: Human light chain FR2
<220> FEATURE:
<221> NAME/KEY: VARIANT
<222> LOCATION: (8)..(9)
<223> OTHER INFORMATION: Xaa can be any naturally occurring amino acid

<400> SEQUENCE: 26

Trp Tyr Gln Gln Lys Pro Gly Xaa Xaa Pro Lys Leu Leu Ile Tyr
1               5                   10                  15

<210> SEQ ID NO 27
<211> LENGTH: 32
<212> TYPE: PRT
<213> ORGANISM: Homo sapiens
<220> FEATURE:
<221> NAME/KEY: DOMAIN
<222> LOCATION: (1)..(32)
<223> OTHER INFORMATION: Human light chain FR3
<220> FEATURE:
<221> NAME/KEY: VARIANT
<222> LOCATION: (4)..(4)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Xaa can be any naturally occurring amino acid
<220> FEATURE:
<221> NAME/KEY: VARIANT
<222> LOCATION: (24)..(25)
<223> OTHER INFORMATION: Xaa can be any naturally occurring amino acid
<220> FEATURE:
<221> NAME/KEY: VARIANT
<222> LOCATION: (27)..(27)
<223> OTHER INFORMATION: Xaa can be any naturally occurring amino acid

<400> SEQUENCE: 27

Gly Val Pro Xaa Arg Phe Thr Gly Xaa Gly Ser Gly Thr Asp Phe Thr
1               5                   10                  15

Leu Thr Ile Ser Ser Leu Gln Xaa Xaa Asp Xaa Ala Thr Tyr Tyr Cys
            20                  25                  30

<210> SEQ ID NO 28
<211> LENGTH: 10
<212> TYPE: PRT
<213> ORGANISM: Homo sapiens
<220> FEATURE:
<221> NAME/KEY: DOMAIN
<222> LOCATION: (1)..(10)
<223> OTHER INFORMATION: Human light chain FR4

<400> SEQUENCE: 28

Phe Gly Ser Gly Thr Lys Leu Glu Ile Lys
1               5                   10

<210> SEQ ID NO 29
```

```
<211> LENGTH: 107
<212> TYPE: PRT
<213> ORGANISM: Mus musculus
<220> FEATURE:
<221> NAME/KEY: DOMAIN
<222> LOCATION: (1)..(107)
<223> OTHER INFORMATION: Amino acid sequence of the light chain variable
      region of 6H8

<400> SEQUENCE: 29

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 30
<211> LENGTH: 321
<212> TYPE: DNA
<213> ORGANISM: Mus musculus
<220> FEATURE:
<221> NAME/KEY: V_region
<222> LOCATION: (1)..(321)
<223> OTHER INFORMATION: Nucleic acid sequence of the light chain
      variable region of 6H8

<400> SEQUENCE: 30
aacattgtaa tgacccaatc tcccaaatcc atgtccatgt cagtgggcga gagggtcacc      60
ttgagctgca aggccagtga gaatgtgggt acttatgtat cctggtatca acagaaacca     120
gagcagtctc ctaaactgct gatatacggg gcatccaacc ggtacactgg ggtccccgat     180
cgcttcacag gcagtggatc tgcaacagat ttcactctga ccatcagcag tgtgcaggct     240
gaagaccttg cagattatca ctgtggacag agttacagct atccattcac gttcggctcg     300
gggacaaagt tggaaataaa a                                               321

<210> SEQ ID NO 31
<211> LENGTH: 116
<212> TYPE: PRT
<213> ORGANISM: Mus musculus
<220> FEATURE:
<221> NAME/KEY: DOMAIN
<222> LOCATION: (1)..(116)
<223> OTHER INFORMATION: Amino acid sequence of heavy chain variable
      region of 6H8

<400> SEQUENCE: 31

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Phe
            20                  25                  30

Trp Met Asn Trp Val Arg Gln Ser Pro Glu Lys Gly Leu Glu Trp Val
        35                  40                  45
```

```
Ala Glu Ile Arg Leu Lys Ser Asn Asn Tyr Ala Thr His Tyr Ala Glu
 50                  55                  60
Ser Val Lys Gly Arg Phe Thr Ile Ser Arg Asp Asp Ser Lys Ser Ser
 65                  70                  75                  80
Val Tyr Leu Gln Met Asn Asn Leu Arg Thr Glu Asp Thr Gly Ile Tyr
                 85                  90                  95
Tyr Cys Thr Ser Tyr Asp Tyr Glu Tyr Trp Gly Gln Gly Thr Leu Val
            100                 105                 110
Thr Val Ser Ala
        115
```

<210> SEQ ID NO 32
<211> LENGTH: 348
<212> TYPE: DNA
<213> ORGANISM: Mus musculus
<220> FEATURE:
<221> NAME/KEY: V_region
<222> LOCATION: (1)..(348)
<223> OTHER INFORMATION: Nucleic acid sequence of the heavy chain variable region of 6H8

<400> SEQUENCE: 32

```
gaagtgaagc ttgaggagtc tggaggaggc ttggtgcaac ctggaggatc catgaaactc      60
tcctgtgttg cctctggatt cactttcagt aacttctgga tgaactgggt ccgccagtct     120
ccagagaagg ggcttgagtg ggttgctgaa attagattga atctaataa ttatgcaaca     180
cattatgcgg agtctgtgaa agggaggttc accatctcaa gagatgattc caaaagtagt     240
gtctacctgc agatgaacaa cttaagaact gaagacactg gcatttatta ctgtaccagc     300
tatgattacg aatactgggg ccaagggact ctggtcaccg tctctgca                 348
```

<210> SEQ ID NO 33
<211> LENGTH: 38
<212> TYPE: DNA
<213> ORGANISM: Artificial Sequence
<220> FEATURE:
<223> OTHER INFORMATION: pFL-6H8-F1

<400> SEQUENCE: 33

```
cccagccggc catggccgaa gtgaagcttg aggagtct                             38
```

<210> SEQ ID NO 34
<211> LENGTH: 34
<212> TYPE: DNA
<213> ORGANISM: Artificial Sequence
<220> FEATURE:
<223> OTHER INFORMATION: linker-R1

<400> SEQUENCE: 34

```
caaagttgga aataaaagcg gccgcagaac aaaa                                 34
```

<210> SEQ ID NO 35
<211> LENGTH: 34
<212> TYPE: DNA
<213> ORGANISM: Artificial Sequence
<220> FEATURE:
<223> OTHER INFORMATION: linker-F1

<400> SEQUENCE: 35

```
ttttgttctg cggccgcttt tatttccaac tttg                                 34
```

<210> SEQ ID NO 36
<211> LENGTH: 34

<210> SEQ ID NO 36
<211> LENGTH: 34
<212> TYPE: DNA
<213> ORGANISM: Artificial Sequence
<220> FEATURE:
<223> OTHER INFORMATION: pFL-6H8-R2

<400> SEQUENCE: 36
ttttgttctg cggccgcttt tatttccaac tttg                          34

<210> SEQ ID NO 37
<211> LENGTH: 37
<212> TYPE: DNA
<213> ORGANISM: Artificial Sequence
<220> FEATURE:
<223> OTHER INFORMATION: 6H8-L1-F1

<400> SEQUENCE: 37
cagccggcca tggccgaagt gcagcttgtg gagtctg                       37

<210> SEQ ID NO 38
<211> LENGTH: 53
<212> TYPE: DNA
<213> ORGANISM: Artificial Sequence
<220> FEATURE:
<223> OTHER INFORMATION: 6H8-L1-F2
<220> FEATURE:
<221> NAME/KEY: misc_feature
<222> LOCATION: (34)..(35)
<223> OTHER INFORMATION: R = G or A, S = G or C

<400> SEQUENCE: 38
cgccaggctc cagggaaggg gcttgagtgg gttrscgaaa ttagattgaa atc     53

<210> SEQ ID NO 39
<211> LENGTH: 50
<212> TYPE: DNA
<213> ORGANISM: Artificial Sequence
<220> FEATURE:
<223> OTHER INFORMATION: 6H8-L1-F3
<220> FEATURE:
<221> NAME/KEY: misc_feature
<222> LOCATION: (17)..(17)
<223> OTHER INFORMATION: R = G or A

<400> SEQUENCE: 39
cagatgaact ccttaargac tgaagacact gccgtgtatt actgtaccag         50

<210> SEQ ID NO 40
<211> LENGTH: 48
<212> TYPE: DNA
<213> ORGANISM: Artificial Sequence
<220> FEATURE:
<223> OTHER INFORMATION: 6H8-L1-R1
<220> FEATURE:
<221> NAME/KEY: misc_feature
<222> LOCATION: (21)..(21)
<223> OTHER INFORMATION: M = A or C
<220> FEATURE:
<221> NAME/KEY: misc_feature
<222> LOCATION: (32)..(32)
<223> OTHER INFORMATION: Y = T or C

<400> SEQUENCE: 40
gaaagtgaat ccagaggcgg macaggagag cytcagggat cctccagg           48

<210> SEQ ID NO 41
<211> LENGTH: 53
<212> TYPE: DNA
<213> ORGANISM: Artificial Sequence
<220> FEATURE:

<223> OTHER INFORMATION: 6H8-L1_R2

<400> SEQUENCE: 41
ccctggagcc tggcggaccc agttcatcca gaagttactg aaagtgaatc cag    53

<210> SEQ ID NO 42
<211> LENGTH: 47
<212> TYPE: DNA
<213> ORGANISM: Artificial Sequence
<220> FEATURE:
<223> OTHER INFORMATION: 6H8-L1-R3
<220> FEATURE:
<221> NAME/KEY: misc_feature
<222> LOCATION: (36)..(36)
<223> OTHER INFORMATION: R = G or A
<220> FEATURE:
<221> NAME/KEY: misc_feature
<222> LOCATION: (39)..(39)
<223> OTHER INFORMATION: K = G or T

<400> SEQUENCE: 42
taaggagttc atctgcaggt acaggrtgkt tttggaatca tctcttg    47

<210> SEQ ID NO 43
<211> LENGTH: 38
<212> TYPE: DNA
<213> ORGANISM: Artificial Sequence
<220> FEATURE:
<223> OTHER INFORMATION: 6H8-L1-R

<400> SEQUENCE: 43
gggagattgg gtcatctgaa tgtcgctagc accgccac    38

<210> SEQ ID NO 44
<211> LENGTH: 49
<212> TYPE: DNA
<213> ORGANISM: Artificial Sequence
<220> FEATURE:
<223> OTHER INFORMATION: 6H8-L1_R5
<220> FEATURE:
<221> NAME/KEY: misc_feature
<222> LOCATION: (23)..(24)
<223> OTHER INFORMATION: R = G or A, S = G or C
<220> FEATURE:
<221> NAME/KEY: misc_feature
<222> LOCATION: (33)..(33)
<223> OTHER INFORMATION: W = A or T
<220> FEATURE:
<221> NAME/KEY: misc_feature
<222> LOCATION: (36)..(36)
<223> OTHER INFORMATION: V = G or C or A

<400> SEQUENCE: 44
ggtgaccctg tcgcccactg agrsggacag ggwggvggga gattgggtc    49

<210> SEQ ID NO 45
<211> LENGTH: 39
<212> TYPE: DNA
<213> ORGANISM: Artificial Sequence
<220> FEATURE:
<223> OTHER INFORMATION: 6H8-L1_F4
<220> FEATURE:
<221> NAME/KEY: misc_feature
<222> LOCATION: (19)..(19)
<223> OTHER INFORMATION: M = A or C
<220> FEATURE:
<221> NAME/KEY: misc_feature
<222> LOCATION: (22)..(22)
<223> OTHER INFORMATION: W = A or T

<400> SEQUENCE: 45

```
gtgggcgaca gggtcaccmt cwcctgcaag gccagtgag                     39
```

<210> SEQ ID NO 46
<211> LENGTH: 53
<212> TYPE: DNA
<213> ORGANISM: Artificial Sequence
<220> FEATURE:
<223> OTHER INFORMATION: 6H8-L1_F6
<220> FEATURE:
<221> NAME/KEY: misc_feature
<222> LOCATION: (15)..(15)
<223> OTHER INFORMATION: Y = T or C
<220> FEATURE:
<221> NAME/KEY: misc_feature
<222> LOCATION: (20)..(20)
<223> OTHER INFORMATION: S = G or C
<220> FEATURE:
<221> NAME/KEY: misc_feature
<222> LOCATION: (24)..(24)
<223> OTHER INFORMATION: W = A or T

<400> SEQUENCE: 46

```
tcagcagtct gcagyccgas gacwtcgcaa cctattactg tggacagagt tac     53
```

<210> SEQ ID NO 47
<211> LENGTH: 50
<212> TYPE: DNA
<213> ORGANISM: Artificial Sequence
<220> FEATURE:
<223> OTHER INFORMATION: 6H8-L1_F5

<400> SEQUENCE: 47

```
ccggcagtgg atctggcaca gatttcactc tgaccatcag cagtctgcag         50
```

<210> SEQ ID NO 48
<211> LENGTH: 51
<212> TYPE: DNA
<213> ORGANISM: Artificial Sequence
<220> FEATURE:
<223> OTHER INFORMATION: 6H8-L1_R6
<220> FEATURE:
<221> NAME/KEY: misc_feature
<222> LOCATION: (33)..(33)
<223> OTHER INFORMATION: H = A or C or T
<220> FEATURE:
<221> NAME/KEY: misc_feature
<222> LOCATION: (36)..(36)
<223> OTHER INFORMATION: K = G or T

<400> SEQUENCE: 48

```
gttggatgcc ccgtatatca gcagtttagg gghctkgcct ggtttctgtt g       51
```

<210> SEQ ID NO 49
<211> LENGTH: 37
<212> TYPE: DNA
<213> ORGANISM: Artificial Sequence
<220> FEATURE:
<223> OTHER INFORMATION: 6H8-L1_R8

<400> SEQUENCE: 49

```
tttgttctgc ggccgctttt atttccaact ttgtccc                       37
```

<210> SEQ ID NO 50
<211> LENGTH: 54
<212> TYPE: DNA
<213> ORGANISM: Artificial Sequence
<220> FEATURE:
<223> OTHER INFORMATION: 6H8-L1_R7
<220> FEATURE:

```
<221> NAME/KEY: misc_feature
<222> LOCATION: (15)..(15)
<223> OTHER INFORMATION: W = A or T
<220> FEATURE:
<221> NAME/KEY: misc_feature
<222> LOCATION: (24)..(24)
<223> OTHER INFORMATION: M = A or C

<400> SEQUENCE: 50
agatccactg ccggwgaagc gggmggggac cccagtgtac cggttggatg cccc      54

<210> SEQ ID NO 51
<211> LENGTH: 39
<212> TYPE: DNA
<213> ORGANISM: Artificial Sequence
<220> FEATURE:
<223> OTHER INFORMATION: PCI-wbp229_F1

<400> SEQUENCE: 51
gctccccggg gcgcgctgtg acattcagat gacccaatc                       39

<210> SEQ ID NO 52
<211> LENGTH: 42
<212> TYPE: DNA
<213> ORGANISM: Artificial Sequence
<220> FEATURE:
<223> OTHER INFORMATION: pCI-6H8_R8

<400> SEQUENCE: 52
ggtgcagcca ccgtacgttt tatttccaac tttgtccccg ag                   42

<210> SEQ ID NO 53
<211> LENGTH: 41
<212> TYPE: DNA
<213> ORGANISM: Artificial Sequence
<220> FEATURE:
<223> OTHER INFORMATION: PCI-wbp229_F2

<400> SEQUENCE: 53
ctctccacag gtgtacactc cgaagtgcag cttctggagt c                    41

<210> SEQ ID NO 54
<211> LENGTH: 41
<212> TYPE: DNA
<213> ORGANISM: Artificial Sequence
<220> FEATURE:
<223> OTHER INFORMATION: PCI-wbp229_F3

<400> SEQUENCE: 54
ctctccacag gtgtacactc cgaagtgcag cttgtggagt c                    41

<210> SEQ ID NO 55
<211> LENGTH: 53
<212> TYPE: DNA
<213> ORGANISM: Artificial Sequence
<220> FEATURE:
<223> OTHER INFORMATION: 6H8-L1_R2

<400> SEQUENCE: 55
ccctggagcc tggcggaccc agttcatcca gaagttactg aaagtgaatc cag       53

<210> SEQ ID NO 56
<211> LENGTH: 49
<212> TYPE: DNA
<213> ORGANISM: Artificial Sequence
<220> FEATURE:
<223> OTHER INFORMATION: 6H8-L1_R5
```

<400> SEQUENCE: 56
ggtgaccctg tcgcccactg agrsggacag ggwggvggga gattgggtc    49

<210> SEQ ID NO 57
<211> LENGTH: 39
<212> TYPE: DNA
<213> ORGANISM: Artificial Sequence
<220> FEATURE:
<223> OTHER INFORMATION: PCI-wbp229_R1

<400> SEQUENCE: 57
gggcccttgg tcgacgctgc agagacagtg accagagtc    39

<210> SEQ ID NO 58
<211> LENGTH: 116
<212> TYPE: PRT
<213> ORGANISM: Artificial Sequence
<220> FEATURE:
<223> OTHER INFORMATION: Synthetic

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ser Tyr Asp Tyr Glu Tyr Trp Gly Gln Gly Thr Leu Val
            100                 105                 110

Thr Val Ser Ala
        115
```

<210> SEQ ID NO 59
<211> LENGTH: 116
<212> TYPE: PRT
<213> ORGANISM: Artificial Sequence
<220> FEATURE:
<223> OTHER INFORMATION: Synthetic

<400> SEQUENCE: 59

```
Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Asn Phe
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ile
65                  70                  75                  80

Leu Tyr Leu Gln Met Asn Ser Leu Arg Thr Glu Asp Thr Val Tyr
                85                  90                  95
```

```
Tyr Cys Thr Ser Tyr Asp Glu Tyr Trp Gly Gln Gly Thr Leu Val
                100                 105                 110

Thr Val Ser Ala
        115

<210> SEQ ID NO 60
<211> LENGTH: 107
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ser Thr Leu Ser Ala Ser Val Gly
1               5                   10                  15

Asp Arg Val Thr Leu Ser Cys Lys Ala Ser Glu Asn Val Gly Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: Synthetic

<400> SEQUENCE: 61

Asp Ile Gln Met Thr Gln Ser Pro Pro Ser Leu Ser Leu Ser Val Gly
1               5                   10                  15

Asp Arg Val Thr Ile Thr Cys Lys Ala Ser Glu Asn Val Gly Thr Tyr
            20                  25                  30

Val Ser Trp Tyr Gln Gln Lys Pro Gly Gln Thr Pro Lys Leu Leu Ile
        35                  40                  45

Tyr Gly Ala Ser Asn Arg Tyr Thr Gly Val Pro Ser Arg Phe Ser Gly
    50                  55                  60

Thr Gly Ser Gly Thr Asp Phe Thr Leu Thr Ile Ser Ser Leu Gln Ser
65                  70                  75                  80

Asp Asp Ile Ala Thr Tyr Tyr Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: Synthetic

<400> SEQUENCE: 62

Asp Ile Gln Met Thr Gln Ser Pro Ala Thr Leu Ser Val Ser Val Gly
```

-continued

```
1               5                   10                  15
Asp Arg Val Thr Leu Ser Cys Lys Ala Ser Glu Asn Val Gly Thr Tyr
            20                  25                  30

Val Ser Trp Tyr Gln Gln Lys Pro Gly Lys Ser Pro Lys Leu Leu Ile
            35                  40                  45

Tyr Gly Ala Ser Asn Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Ser Tyr Ser Tyr Pro Phe
                85                  90                  95

Thr Phe Gly Ser Gly Thr Lys Leu Glu Ile Lys
                100                 105
```

HUMANIZED ANTI-BASIGIN ANTIBODIES AND THE USE THEREOF

FIELD OF THE INVENTION

The present disclosure generally relates to humanized anti-BASIGIN antibodies and the use thereof.

BACKGROUND

BASIGIN (also known as EMMPRIN, Neurothelin and M6 antigen) is a highly glycosylated transmembrane glycoprotein with a molecular weight of 50 to 60 kD and is a member of the immunoglobulin superfamily (IgSF). In humans, BASIGIN has 269 amino acids, which can be divided into extracellular, transmembrane and intracellular regions, wherein the first 21 residues from N-terminal translation start point constitute signal peptide, residues 22-205 constitute extracellular domain, residues 206-229 constitute transmembrane region with typical leucine zipper structure, residues 230-269 at C-terminal constitute intracellular domain.

It has been shown that BASIGIN is overexpressed in many types of human solid tumors such as lung cancer, liver cancer, cervical cancer, colon cancer, breast cancer, ovarian cancer, esophageal cancer or gastric cancer. Previous studies have shown that BASIGIN molecules are important functional membrane proteins in tumor progression and are involved in a variety of cancer-related phenomena such as the following:

i. BASIGIN mediates the adhesion and metastasis of tumor cells. BASIGIN expressed on the surface of tumor cells interacts with vinclin to promote pseudopodia formation, spread and adhesion of tumor cells; interacts with annexin II to promote the secretion of MMP-2 in tumor cells; accelerates the degradation of the surrounding matrix and promotes the tumor metastasis through stimulating tumor cells and fibroblasts around tumor cells to secret various extracellular matrix metalloproteinase (MMP), for example MMP-1, MMP-2, MMP-3, MMP-11, MT1-MMP and MT2-MMP etc.

ii. BASIGIN is involved in the anaerobic metabolism of tumor cells. BASIGIN is an important molecular chaperone of monocarboxylate transporter MCT-1 and MCT-4. BASIGIN can interact with MCT-1 and MCT-4 to assist their correct positioning on the cell membrane and continue to regulate their transportation of lactate metabolites. As the tumor cells rely mainly on anaerobic metabolism to produce energy, BASIGIN regulates the energy metabolism and the function of tumor cells indirectly through the expression of MCTs.

iii. BASIGIN promotes drug-resistance of tumor cells. BASIGIN affects the transcription of multidrug resistance (MDR) gene and promotes the expression of P-g by co-expression regulation mechanism, and consequently induces the MDR of tumor. Kanekura et al. proved that BASIGIN causes MDR via P-g, indicating BASIGIN may be a potential effective target for inhibiting MDR. In addition, BASIGIN promotes the nuclei localization of p-TFII-I and up-regulates the expression of Bip, a key factor in the unfolded protein response (UPR), leading to endoplasmic reticulum stress and UPR in tumor cells, thereby inhibiting apoptosis and resulting in drug insensitivity. Inhibition of BASIGIN can promote apoptosis of hepatocellular carcinoma cells and enhance the sensitivity of tumor cells to existing antitumor drugs.

iv. BASIGIN upregulates VEGF expression to promote tumor angiogenesis. Therefore, inhibition of BASIGIN expression can significantly inhibit the secretion of VEGF and thereby inhibit tumor angiogenesis.

v. BASIGIN interacts with multiple molecules. The transmembrane region of BASIGIN protein has a highly conserved negatively charged glutamate, which is the structural basis for its interaction with a variety of cell membrane proteins, and also suggests that BASIGIN can affect a variety of physiological activities of cells via interactions with a variety of proteins. BASIGIN interacts with CD98, Integrin, caveolin-1, cyclophilins (CyP) and other proteins to affect the growth and metastasis of tumor cells by modulating cell functions such as energy metabolism, cell-matrix interaction, signal transduction etc.

In addition, a number of retrospective studies have shown a close correlation between the expression level of BASIGIN in the tumor tissue and the prognosis of cancer patients. In non-small cell lung cancer patients, BASIGIN expression levels and the patient's prognosis is closely related.

Therefore, BASIGIN has become a new target for tumor therapy, and the successful development of antibody drug LICARTIN ($^{131}$I-labeled CD147-specific antibody metuximab) proved the safety and effectiveness of the drugs targeting BASIGIN.

In addition, the interaction between BASIGIN expressed on erythrocytes and rhoptry protein PfRh5 of *Plasmodium falciparum* in a ligand-receptor manner mediates the distal recognition of erythrocytes by *Plasmodium falciparum*, which is a key element in the invasion of *Plasmodium falciparum*. The interaction between PfRh5 and BASIGIN on erythrocytes is in different malaria strains, suggesting that BASIGIN on erythrocytes are expected to be important targets for antimalarial drugs. The new antimalarial drug against human BASIGIN on erythrocyte is used in combination with traditional antimalarial drugs to overcome the resistance against chemotherapeutic drugs.

Monoclonal antibody (McAb) has been widely used in the diagnosis and treatment of diseases. However, multiple injection of murine McAb into the human body may result in human anti-mouse antibody (HAMA) reaction in the patient, systemic allergic reactions may block the effectiveness of antibody. Therefore, human antibodies and humanized antibodies are studied in antibody drug research and development to explore their potential advantages.

BRIEF SUMMARY OF THE INVENTION

The present disclosure provides humanized anti-BASIGIN antibodies with high binding affinity, and the biological activity is verified through experiments.

The present disclosure provides a humanized anti-BASIGIN antibody or antigen binding fragment thereof, which comprises a heavy chain variable region ($V_H$).

In some embodiments, the $V_H$ has an amino acid sequence of SEQ ID NO: 1 (EVQLXESGGGLVQPGGSLRLSCXASGFTFSNFWMNWVRQAPGKGLEWVXE IRLKSNNYATHYAESVKGRFTISRDDSKXXLYLQMNSLXTEDTXVYYCTSYD YEYWGQGTLVTVSA), wherein the X at position i (i=5, 23, 49, 79, 80, 89, 94) of SEQ ID NO: 1 is referred as $X_{Hi}$, each of $X_{H5}$, $X_{H23}$, $X_{H49}$, $X_{H79}$, $X_{H80}$, $X_{H89}$, $X_{H94}$ can be any amino acid.

In some embodiments, $X_{H5}$ is V or L. In some embodiments, $X_{H23}$ is A or S. In some embodiments, $X_{H49}$ is S, A or G. In some embodiments, $X_{H79}$ is N or S. In some embodiments, $X_{H80}$ is T or I. In some embodiments, $X_{H89}$ is K or R. In some embodiments, $X_{H94}$ is A or T.

In some embodiments, (a) $X_{H5}$ is V, $X_{H23}$ is A; and/or (b) $X_{H49}$ is S or A; and/or (c) $X_{H79}$ is N, $X_{H50}$ is T, $X_{H89}$ is K or R, $X_{H94}$ is A.

In some embodiments, the $V_H$ comprises three heavy chain CDRs as set forth in SEQ ID NO: 9-11.

In some embodiments, the $V_H$ comprises framework regions (FRs) as set forth in SEQ ID NO:12, SEQ ID NO:13, SEQ ID NO:14, and SEQ ID NO:15.

In some embodiments, the $V_H$ has an amino acid sequence of SEQ ID NO:3, SEQ ID NO:5 or SEQ ID NO:7.

In some embodiments, the humanized anti-BASIGIN antibody or antigen binding fragment thereof further comprises a light chain variable region ($V_L$).

In some embodiments, the $V_L$ has an amino acid sequence of SEQ ID NO: 2 (DIQMTQSPXXLSXSVGDRVTXXCKA-SENVGTYVSWYQQKPGXXPKLLIYGA SNRYTGVPXRFTGXGSGTDFTLTISSLQXXDX-ATYYCGQSYSYPFTFGSGTKL EIK), wherein the X at position j (j=9, 10, 13, 21, 22, 42, 43, 60, 65, 80, 81, 83) of SEQ ID NO: 2 is referred as $X_{Lj}$, each of $X_{L9}$, $X_{L10}$, $X_{L13}$, $X_{L21}$, $X_{L22}$, $X_{L42}$, $X_{L43}$, $X_{L60}$, $X_{L65}$, $X_{L80}$, $X_{L81}$, $X_{L83}$ can be any amino acid.

In some embodiments, $X_{L9}$ is S, P or A. In some embodiments, $X_{L10}$ is T or S. In some embodiments, $X_{L13}$ is A, L or V. In some embodiments, $X_{L21}$ is L or I. In some embodiments, $X_{L22}$ is S or, T. In some embodiments, $XL_{42}$ is K or Q. In some embodiments, $X_{L43}$ is A, T or S. In some embodiments, $X_{L80}$ is S or A. In some embodiments, $X_{L65}$ is S or T. In some embodiments, $X_{L80}$ is P or S. In some embodiments, $X_{L81}$ is E or D. In some embodiments, $X_{L83}$ is F or I.

In some embodiments, (a) $X_{L9}$ is S or A, $X_{L10}$ is T or S, $X_{L13}$ is A, $X_{L21}$ is L or I, $X_{L22}$ is S or T; (b) $X_{L42}$ is K or Q, $X_{L43}$ is A or T; and/or (c) $X_{L60}$ is S, $X_{L65}$ is S or T, $X_{L80}$ is P, $X_{L81}$ is E or D, $X_{L83}$ is F.

In some embodiments, the $V_L$ comprises three light chain CDRs as set forth in SEQ ID NO. 22-24.

In some embodiments, the $V_L$ comprises FRs as set forth in SEQ ID NO:25, SEQ ID NO:26, SEQ ID NO:27, and SEQ ID NO:28.

In some embodiments, the $V_L$ has an amino acid sequence of SEQ ID NO:16, SEQ ID NO:18 or SEQ ID NO:20.

In some embodiments, the antigen binding fragment is an antibody fragment selected from F(ab')$_2$, Fab', Fab, Fv, scFv, dsFv, dAb, and a single chain binding polypeptide.

In some embodiments, the humanized anti-BASIGIN antibody or antigen binding fragment thereof comprises a constant region of human IgG heavy chain. In some embodiments, the human IgG is human IgG2. In some embodiments, the humanized anti-BASIGIN antibody or antigen binding fragment thereof comprises a constant region of human κ chain.

In some embodiments, the humanized anti-BASIGIN antibody or antigen binding fragment thereof binds to BASIGIN with a $K_D$ between about $1\times10^{-11}$ M and about $5\times10^{-10}$ M or between about $5\times10^{-11}$ M and about $1.1\times10^{-10}$ M.

In one aspect, the present disclosure also provides an isolated nucleic acid sequence encoding the humanized anti-BASIGIN antibody or antigen binding fragment thereof provided herein.

In some embodiments, the isolated nucleic acid sequence comprises a nucleotide sequence of SEQ ID NO:4, SEQ ID NO:6, SEQ ID NO:8, SEQ ID NO:17, SEQ ID NO: 19, or SEQ ID NO:21.

In another aspect, the present disclosure also provides a vector comprising the nucleic acid sequence encoding the humanized anti-BASIGIN antibody or antigen binding fragment thereof provided herein.

In another aspect, the present disclosure provides a host cell comprising the vector provided herein. In some embodiments, the host cell is CHO cell.

In yet another aspect, the present disclosure provides a composition comprising the humanized anti-BASIGIN antibody or antigen binding fragment thereof provided herein and a pharmaceutically acceptable carrier.

In another aspect, the present disclosure provides a method of treating a BASIGIN related condition in a subject, which comprises administering an effective amount of the composition provided herein to the subject.

In some embodiments, the BASIGIN related condition is cancer or malaria. In some embodiments, the cancer is lung cancer, liver cancer, cervical cancer, colon cancer, breast cancer, ovarian cancer, esophageal cancer or gastric cancer. In some embodiments, the subject is human.

In another aspect, the present disclosure provides use of the humanized anti-BASIGIN antibody or antigen binding fragment thereof provided herein in the manufacture of a medicament for treating a BASIGIN related condition in a subject.

BRIEF DESCRIPTION OF FIGURES

FIG. 1 is a graphic illustration showing certain illustrative variations at specific amino acids sites in the heavy chain FRs of the humanized anti-BASIGIN antibodies. The line of "mouse" show the amino acid sequence of heavy chain variable region of 6H8 (SEQ ID NO: 31). In the line of "human", the preferred amino acids at each indicated specific site in heavy chain FRs are listed. The figure also shows three illustrative amino acid sequences (SEQ ID NO: 58, SEQ ID NO: 59, and SEQ ID NO: 3) of the heavy chain variable region.

FIG. 2 is a graphic illustration showing certain illustrative variations at specific amino acids sites in the light chain FRs of the humanized anti-BASIGIN antibodies. The line of "mouse" show the amino acid sequence of light chain variable region of 6H8 (SEQ ID NO: 29). In the line of "human", the preferred amino acids at each indicated specific site in light chain FRs are listed. The figure also shows three illustrative amino acid sequences (SEQ ID NO: 60, SEQ ID NO: 61, and SEQ ID NO: 62) of the light chain variable region.

DETAILED DESCRIPTION OF THE INVENTION

Figure 3:
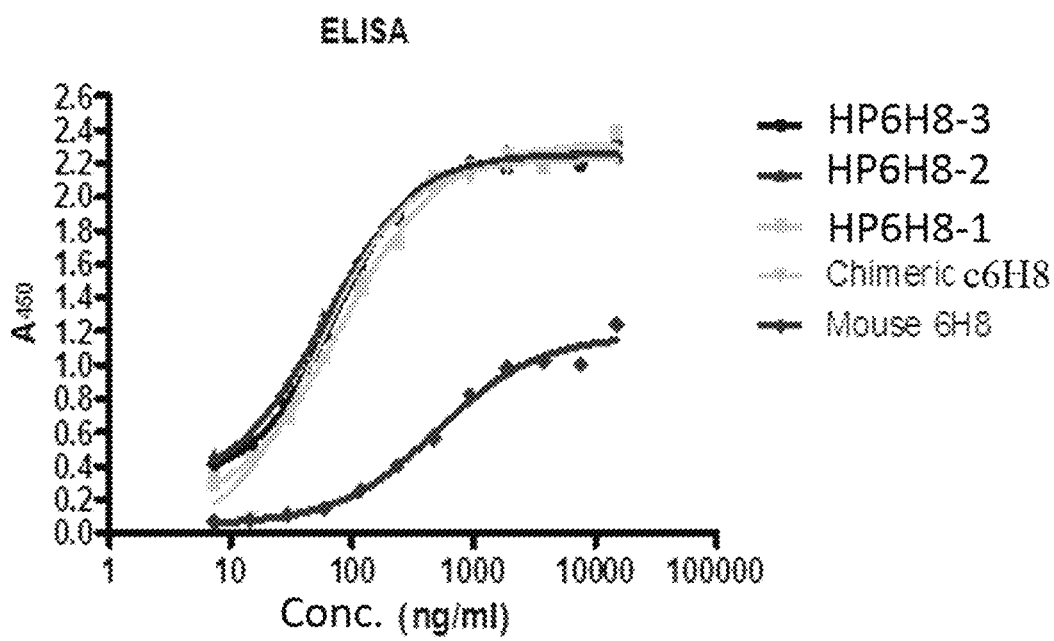
FIG. 3 shows the dose-dependent binding of anti-BASIGIN antibodies including mouse 6H8 (solid diamond), chimeric 6H8 (inverted solid triangle), humanized HP6H8-1 (solid circle), humanized HP6H8-2 (solid triangle), humanized HP6H8-3 (solid square) to human BASIGIN as measured by ELISA analysis.

The following description of the present disclosure is merely intended to illustrate various embodiments of the present disclosure. As such, the specific modifications discussed are not to be construed as limitations on the scope of the present disclosure. It will be apparent to one skilled in the art that various equivalents, changes, and modifications may be made without departing from the scope of the present disclosure, and it is understood that such equivalent embodiments are to be included herein. All references cited herein, including publications, patents and patent applications are incorporated herein by reference in their entirety.

Humanized Anti-BASIGIN Antibody or Antigen Binding Fragment Thereof

In one aspect, the present disclosure provides a humanized anti-BASIGIN antibody or antigen binding fragment thereof.

As used herein, the term "antibody" as used herein includes any immunoglobulin, monoclonal antibody, multivalent antibody, multispecitic antibody, or bispecific (bivalent) antibody. A native intact antibody comprises two heavy chains (H) and two light chains (L) inter-connected by disulfide bonds. Each heavy chain of an antibody consists of a variable region ($V_H$) and a first, second, and third constant region ($C_{H1}$, $C_{H2}$, $C_{H3}$, respectively), while each light chain of the antibody consists of a variable region ($V_L$) and a constant region ($C_L$) The variable regions of the light and heavy chains are responsible for antigen binding. The variables region in both chains are generally subdivided into three regions of hypervariability called the complementarity determining regions (CDRs) (wherein, light (L) chain CDRs including LCDR1, LCDR2 and LCDR3, and heavy (H) chain CDRs including HCDR1, HCDR2, HCDR3). CDR boundaries for the antibodies and antigen binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 31(6252):877-83 (1989); Kabat E. A. et al., National Institutes of Health, Bethesda, Md (1991)). In some embodiments, the CDR boundaries of an antibody are determined according to Kabat database. The three CDRs are interposed between flanking stretches known as framework regions (FRs, wherein heavy (H) chain FRs including HFR1, HFR2, HFR3 and HFR4, and light (L) chain FRs including LFR1, LFR2, LFR3 and LFR4), which are more highly conserved than the CDRs and form a scaffold to support the hypervariable loops. Therefore, each $V_H$ and $V_L$ comprises three CDRs and four FRs in the following order (amino acid residues N terminus to C terminus): FR1, CDR1, FR2, CDR2, FR3, CDR3, FR4. The constant regions of the heavy and light chains are not involved in antigen binding, but exhibit various effector functions.

Mammalian heavy chains are classified as α, δ, ε, γ, and μ, and mammalian light chains are classified as λ or κ. Antibodies are assigned to the five major classes based on the amino acid sequence of the constant region of their heavy chain: IgA, IgD, IgE, IgG, and IgM, which are characterized by the presence of α, δ, ε, γ, and μ heavy chains, respectively. Subclasses of several of the major antibody classes are such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

An antibody or antigen binding fragment that has a portion of heavy and/or light chain derived from one species, and the rest of the heavy and/or light chain derived from a different species is referred to as chimeric. In an illustrative example, a chimeric antibody may comprise a constant region derived from human and a variable region derived from a non-human species, such as from mouse.

A humanized antibody or antigen binding fragment, refers to an antibody or the antigen binding fragment which comprises CDRs derived from non-human (e.g., a rodent, rabbit, dog, goat, horse, or chicken) antibodies, and variable region FRs and constant regions (if present) entirely or substantially from human immunoglobulins.

"Substantially" as used herein refers to a high degree of similarity between two compared items (e.g., sequences, numeric values), and those skilled in the art would not consider there is a significant difference between the two item, and/or would anticipate that the two compared items are of little difference with regard to their properties (e.g., physical properties, or biological activities).

In some embodiments, the sequence of a humanized antibody or antigen binding fragment is altered (e.g., substituted, inserted or deleted) to improve the antibody in one or more properties, such as binding affinity, stability, immunogenicity, pharmacokinetic half-life, pH sensitivity, compatibility to conjugation etc. In some embodiments, one or more amino acid residues in one or more non-human CDRs and/or human FRs is altered to improve one or more above-stated properties of the antibody while maintain or improve the binding affinity of the antibody, wherein the altered amino acid residues either are not critical for specific binding or the alterations are conservative changes, such that the binding of the humanized antibody to BASIGIN is not significantly affected.

In some embodiments, the CDR derived from non-human antibodies may comprise the same amino acid sequence as the non-human CDR from which it is derived, or it may comprise no more than 3, no more than 2, or no more than 1 amino acid alterations. In some embodiments, the alterations are conservative substitutions.

A "conservative substitution" with reference to amino acid sequence refers to replacing an amino acid residue with a different amino acid residue having a side chain with similar physiochemical properties or substitution of those amino acids that are not critical to the activity of the polypeptide. For example, conservative substitutions can be made among amino acid residues with nonpolar side chains (e.g., Met, Ala, Val, Leu, Ile, Pro, Phe and Trp), among residues with uncharged polar side chains (e.g., Cys, Ser, Thr, Asn, Gly and Gin), among residues with acidic side chains (e.g., Asp and Glu), among amino acids with basic side chains (e.g., His, Lys and Arg), among amino acids with beta-branched side chains (e.g., Thr, Val and Ile), among amino acids with sulfur-containing side chains (e.g., Cys and Met), or among residues with aromatic side chains (e.g., Trp, Tyr, His and Phe). In some embodiments, substitutions, deletions or additions can also be considered as "conservative substitution" as long as such substitutions, deletions, or additions does not cause significant change in the protein conformational structure, and therefore could retain the biological activity of a protein. The number of amino acids that are inserted or deleted as a conservative substitution can be in the range of about 1 to 3.

In some embodiments, the humanized anti-BASIGIN antibody or antigen binding fragment thereof comprises a heavy chain variable region ($V_H$). In some embodiments, the $V_H$ comprises CDRs set forth in SEQ ID NO: 9-11. In some embodiments, the humanized anti-BASIGIN antibody or antigen binding fragment thereof comprises a light chain variable region ($V_L$). In some embodiments, the $V_L$ comprises CDRs set forth in SEQ ID NO: 22-24.

In some embodiments, computer software can be used to virtually simulate the binding of the antibodies or the antigen binding fragments to human BASIGIN, and thus identify the amino acid sites on the antibodies/fragments (e.g., FRs) which are not critical for binding. Different amino acids may be tested for such sites in the simulation to identify those do not change the structure/conformation of the binding portion of the antibody or the antigen binding fragment, or optionally improve one or more properties of the antibodies or antigen binding fragments, such as binding or binding affinity, stability, immunogenicity, pharmacokinetic half-life, pH sensitivity, compatibility to conjugation etc. Examples of such computer software include but are not limited to, SYBYL, Discovery Studio, MOE, AMBER, GROMACS, NAMD, CONCOORD, DynDom, Autodock, MODELER, MolMol etc.

In some embodiments, the FR regions of the humanized anti-BASIGIN antibody or antigen binding fragment thereof may comprise some amino acid variations at for example, no more than 20, 19, 18, 17, 16, 15, 14, 13, 12, 11, 10, 9, 8, 7, 6, 5, 4, 3, 2, or 1 amino acid sites. In some embodiments, the FR regions of the humanized anti-BASIGIN antibody or antigen binding fragment thereof are homologous to the non-human FRs.

As used herein, "homologue" and "homologous" are used interchangeable and refer to amino acid sequences or nucleic acid sequences (or its complementary strand) that have sequences identity of at least 80% (e.g., at least 85%, 88%, 90%, 91%, 92%, 93%, 94%, 95%, 96%, 97%, 98%, 99%) to another sequences when optionally aligned.

Percent (%) "sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum correspondence. Alignment for purposes of determining percent amino acid (or nucleic acid) sequence identity can be achieved, for example, by using publicly available tools such as BLASTN, BLASTp, ClustalW2, and ALIGN or Megalign (DNASTAR) software.

In some embodiments, the $V_H$ has an amino acid sequence of SEQ ID NO: 1 (EVQLXESGGGLVQPGGSLRLSCX-ASGFTFSNFWMNWVRQAPGKGLEWVXE IRLKSN-NYATHYAESVKGRFTISRDDSKXXLYLQMNSLXT-EDTXVYYCTSYD YEYWGQGTLVTVSA), wherein the X at position i (i=5, 23, 49, 79, 80, 89, 94) of SEQ ID NO: 1 is referred as $X_{H1}$, each of $X_{H5}$, $X_{H23}$, $X_{H49}$, $X_{H79}$, $X_{H80}$, $X_{H89}$, $X_{H94}$ can be any amino acid. In some embodiments, the $V_H$ consists of an amino acid sequence of SEQ ID NO: 1 (EVQLXESGGGLVQPGGSLRLSCXAS-GFTFSNFWMNWVRQAPGKGLEWVXE IRLKSN-NYATHYAESVKGRFTISRDDSKXXLYLQMNSLrXT-EDTXVYYCTSYD YEYWGQGTLVTVSA), wherein the X at position i (i=5, 23, 49, 79, 80, 89, 94) of SEQ ID NO: 1 is referred as $X_{H1}$, each of $X_{H5}$, $X_{H23}$, $X_{H49}$, $X_{H79}$, $X_{H80}$, $X_{H89}$, $X_{H94}$ Can be any amino acid.

In some embodiments, $X_{H5}$ is V or L. In some embodiments, $X_{H23}$ is A or S. In some embodiments, $X_{H49}$ is S, A or G. In some embodiments, $X_{H79}$ is N or S. In some embodiments, $X_{H80}$ is T or I. In some embodiments, $X_{H89}$ is K or R. In some embodiments, $X_{H94}$ is A or T.

In some embodiments, (a) $X_{H5}$ is V, $X_{V_{H23}}$ is A; and/or (b) $X_{V_{H49}}$ is S or A; and/or (c) $X_{V_{H79}}$ is N, $X_{H80}$ is T, $X_{V_{H89}}$ is K or R, $X_{VH94}$ is A.

In some embodiments, $X_{H5}$ is V, $X_{V_{H23}}$ is A. In some embodiments, $X_{H49}$ is S or A. In some embodiments, $X_{H49}$ is S. In some embodiments, $X_{H49}$ is A. In some embodiments, $X_{H79}$ is N, $X_{H50}$ is T, $X_{H89}$ is K, $X_{H94}$ is A. In some embodiments, $X_{H79}$ is N, $X_{H80}$ is T, $X_{H80}$ is R, $X_{H94}$ is A.

In some embodiments, the $V_H$ comprises one or more heavy chain FRs selected from SEQ ID NO 12-15. In some embodiments, the $V_H$ comprises an amino acid sequence of SEQ ID NO:3, SEQ ID NO:5 or SEQ ID NO:7. In some embodiments, the $V_H$ consists of an amino acid sequence of SEQ ID NO:3, SEQ ID NO:5 or SEQ ID NO:7.

In some embodiments, the humanized anti-BASIGIN antibody or antigen binding fragment thereof comprises a light chain variable region $V_L$. In some embodiments, the $V_L$ comprises CDRs set forth in SEQ ID NO: 22, SEQ ID NO: 23 and SEQ ID NO: 24.

In some embodiments, the $V_L$ has an amino acid sequence of SEQ ID NO: 2 (DIQMTQSPXXLSXSVGDRVTXXCKA-SENVGTYVSWYQQKPGXXPKLLIYGA SNRYTGVPXRFTGXGSGTDFTLTISSLQXXDX-ATYYCGQSYSYPFTFGSGTKL EIK), wherein the X at position j (=9, 10, 13, 21, 22, 42, 43, 60, 65, 80, 81, 83) of SEQ ID NO: 43 is referred as $X_Lj$, each of $X_{L9}$, $X_{L10}$, $X_{L13}$, $X_{L21}$, $X_{L22}$, $X_{L42}$, $X_{L43}$, $X_{L60}$, $XL_{65}$, $X_{L80}$, $X_{L81}$, $X_{L83}$ can be any amino acid. In some embodiments, the $V_L$ consists of an amino acid sequence of SEQ ID NO: 2 (DIQMTQSPXXLSXSVGDRVTXXCKA-SENVGTYVSWYQQKPGXXPKLLIYGA SNRYTGVPXRFTGXGSGTDFTLTISSLQXXDX-ATYYCGQSYSYPFTFGSGTKL EIK), wherein the X at position j j=9, 10, 13, 21, 22, 42, 43, 60, 65, 80, 81, 83) of SEQ ID NO: 43 is referred as $X_{Lj}$, each of $X_{L9}$, $X_{L10}$, $X_{L13}$, $X_{L21}$, $X_{L22}$, $X_{L42}$, $X_{L43}$ $X_{L60}$, $X_{L65}$, $X_{L80}$, $X_{L81}$, $X_{L83}$ can be any amino acid.

In some embodiments, $X_{L9}$ is S, P or A. In some embodiments, $X_{L10}$ is T or S. In some embodiments, $X_{L13}$ is A, L or V. In some embodiments, $XL_{21}$ is L or I. In some embodiments, $X_{L22}$ is S or T. In some embodiments, $X_{L42}$ is K or Q. In some embodiments, $X_{L43}$ is A, T or S. In some embodiments, $X_{L60}$ is S or A. In some embodiments, $X_{L65}$ is S or T. In some embodiments, $X_{L80}$ is P or S. In some embodiments, $X_{L81}$ is E or D. In some embodiments, $X_{L83}$ is F or I.

In some embodiments, (a) $X_{L9}$ is S or A, $X_{L10}$ is T or S, $X_{L13}$ is A, $X_{L21}$ is L or I, $X_{L22}$ is S or T; (b) $X_{L42}$ is K or Q, $X_{L43}$ is A or T; and/or (c) $X_{L60}$ is S, $X_{L65}$ is S or T, $X_{L80}$ is P, $X_{L81}$ is E or D, $X_{L83}$ is F.

In some embodiments, $X_{L9}$ is S, $X_{L10}$ is T, $X_{L13}$ is A, $X_{L21}$ is L, $X_{L22}$ is S. In some embodiments, $X_{L9}$ is A, $X_{L10}$ is S, $X_{VL13}$ is A, $X_{L21}$ is I, $X_{L22}$ is S. In some embodiments, $X_{L9}$ is S, $X_{L10}$ is S, $X_{L13}$ is A, $X_{L21}$ is L, $X_{L22}$ is T.

In some embodiments, $X_{L42}$ is K, $X_{L43}$ is A. In some embodiments, $X_{L42}$ is Q, $X_{L43}$ is T. In some embodiments, $X_{L42}$ is Q, $X_{L43}$ is A.

In some embodiments, $X_{L60}$ is S, $X_{L65}$ is S, $X_{L80}$ is P. $X_{L81}$ is E, $X_{L83}$ is F. In some embodiments, $X_{L60}$ is S, $X_{L65}$ is S, $X_{L80}$ is P, $X_{L81}$ is D, $X_{L83}$ is F.

In some embodiments, the $V_L$ comprises one or more FRs selected from SEQ ID NO: 25-28.

In some embodiments, the $V_L$ comprises an amino acid sequence of SEQ ID NO:16, SEQ ID NO:18 or SEQ ID NO:20. In some embodiments, the $V_L$ consists of an amino acid sequence of SEQ ID NO:16, SEQ ID NO:18 or SEQ ID NO:20.

In some embodiments, the humanized antibodies or antigen binding fragment thereof comprises a heavy chain comprising a constant region of human IgA, IgD, IgE, IgG, or IgM heavy chain. In some embodiments, the heavy chain comprises a constant region of human IgG heavy chain. In some embodiments, the human IgG is human IgG1, IgG2, IgG3, or IgG4. In some embodiments, the human IgG is human IgG2. In some embodiments, the humanized antibodies or fragment thereof comprises a light chain comprising a constant region of human λ or κ chain. In some embodiments, the light chain comprises a constant region of human κ chain.

In some embodiments, the humanized anti-BASIGIN antibody provided herein comprises: three heavy chain CDRs as set forth in SEQ ID NO: 9-11, heavy chain framework sequences of HFR1, HFR2, HFR3 and HFR4 as set forth in SEQ ID NO. 12-15, light chain CDRs as set forth in SEQ ID NO. 22-24 and light chain framework sequences of LFR1, LFR2, LFR3 and LFR4 as set forth in SEQ ID NO: 25-28, wherein the sequences of heavy chain variable region is according to the formula. HFR1-HCDR1-HFR2-CDR2-HFR3-CDR3-HFR4, and the sequences of light chain variable region is according to the formula LFR1-LCDR1-LFR2-LCDR2-LFR3-LCDR3-LFR4.

A humanized antibody or antigen binding fragment is useful as human therapeutics. In some embodiments because it has reduced immunogenicity or is less likely to induce an immune response in human, as compared to the non-human species antibody. In some embodiments, the non-human animal is a mammal, for example, a mouse, a rat, a rabbit, a goat, a sheep, a guinea pig, a hamster, or a non-human primate (for example, a monkey (e.g., cynomolgus or rhesus monkey) or an ape (e.g., chimpanzee, gorilla, simian or affen)).

The term "specific binding" or "specifically binds" as used herein refers to a non-random binding reaction between two molecules, such as for example between an antibody and an antigen. The binding affinity can be represented by $K_D$ value, which is calculated as the ratio of the dissociation rate ($k_{off}$) to the association rate ($k_{on}$), i.e., $k_{off}/k_{on}$, when the binding between the antigen and the antibody reaches equilibrium. The $K_D$ value can be appropriately determined using suitable methods known in the art, including, for example, plasmon resonance binding (SPR) assay using instruments such as Biacore (see, for example, Murphy, M. et al, Current protocols in protein science, Chapter 19, unit 19.14, 2006).

In some embodiments, the anti-BASIGIN antibodies and the antigen binding fragments thereof provided herein are capable of specific binding to human BASIGIN with a binding affinity ($K_D$) of about $10^{-7}$ M or less (e.g., $10^{-8}$ M, $10^{-9}$ M, $10^{-10}$ M, $10^{-11}$ M, $10^{-12}$ M) as measured by plasmon resonance binding assay. In some embodiments, the antibodies or antigen binding fragments provided herein specifically bind human and/or non-human BASIGIN with a binding affinity ($K_D$) of about $1\times10^{-11}$ M to about $1\times10^{-7}$ M, about $1\times10^{-11}$ M to about $1\times10^{-8}$ M, $1\times10^{-11}$ M to about $5\times10^{-9}$ M, about $1\times10^{-11}$ M to about $1\times10^{-9}$ M, $1\times10^{-11}$ M to about $1\times10^{-9}$ M, about $5\times10^{-11}$ M to about $5\times10^{-10}$ M or about $5\times10^{-11}$ M to about $1\times10^{-11}$ M. In some embodiments, the humanized anti-BASIGIN antibody or antigen binding fragment thereof binds to BASIGIN with a $K_D$ between about $1\times10^{-11}$ M and about $5\times10^{-10}$ M, or between about $5\times10^{-11}$ M and about $1.1\times10^{-10}$ M.

In some embodiments, the anti-BASIGIN antibodies and the antigen binding fragments thereof specifically bind to human BASIGIN but not to mouse BASIGIN, for example, the binding affinity with mouse BASIGIN is less than 15%, 10%, 9%, 8%, 7%, 6%, 5%, 4%, 3%, 2%, or 1% of that with human BASIGIN.

As used herein, the term "antigen binding fragment" refers to an antibody fragment formed from a fragment of an antibody comprising one or more CDRs, or any other antibody portion that binds to an antigen but does not comprise an intact native antibody structure. Examples of antigen binding fragment include, without limitation, a Fab, a Fab', a F(ab')$_2$, an Fv fragment, a disulfide stabilized Fv fragment (dsFv), a (dsFv)$_2$, a diabody (dAb), a bispecific ds-diabody (bispecific ds-dAb), a single-chain Fv (scFv), an scFv dimer, a single chain binding polypeptide, an isolated CDR and a multispecific antibody. An antigen binding fragment is capable of binding to the same antigen to which the parent antibody binds.

"Fab" refers to a monovalent antigen binding fragment of the antibody consisting of a single light chain (both variable and constant regions) bound to the variable region and first constant region of a single heavy chain by a disulfide bond.

"Fab'" refers to monovalent antigen binding fragment which corresponds to a Fab fragment further including a portion of the hinge region.

"F(ab')$_2$" refers to a dimer of two Fab' fragments which are bound together by disulfide bonds.

"Fv" consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "(dsFv)$_2$" comprises three peptide chains: two $V_H$ moieties linked by a peptide linker and bound by disulfide bridges to two $V_L$ moieties. In some embodiments, a dsFv is bispecific in which each disulfide paired heavy and light chain has a different antigen specificity.

An "diabody" or "dAb" refers to small fragments with two antigen binding sites, wherein the fragments comprise a $V_H$ domain connected to a $V_L$ domain in a single polypeptide chain ($V_H$-$V_L$ or $V_L$-$V_H$) (see, e.g., Holliger P. et al., Proc Natl Acad Sci USA.; 90(14):6444-8 (1993); EP404097; WO93/11161), by using a linker that is too short to allow pairing between the two domains on the single chain, the domains are forced to pair with the complementary domains of another chain, thereby creating two antigen binding sites.

In some embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

"Single-chain Fv" or "scFv" or "single chain antibody" refers to an engineered antibody fragments comprising a single $V_H$ domain and a single $V_L$ domain of the antibody, wherein these domains are connected to one another directly or via a peptide linker sequence to form a single polypeptide chain (Huston J S et al., Proc Natl Acad Sci USA, 85:5879 (1988)).

A "scFv dimer" refers to a dimer of two scFvs.

A "single chain binding polypeptide" refers to any single chain polypeptide which is capable of binding to an antigen or epitope.

As used herein, the term "antigen" refers to a molecule or a portion of a molecule capable of being bound by an antibody or an antigen binding fragment, and additionally capable of being used in an animal to produce antibodies capable of binding to that antigen. An antigen may possess one or more epitopes. The term "epitope" as used herein refers to the specific group of atoms (e.g., sugar side chains, phosphoryl groups, sulfonyl groups) or amino acids on an antigen that are capable of interacting with antibodies or antigen binding fragments.

In some embodiments, the antigen binding fragment is an antibody fragment selected from Fab, Fab', F(ab')$_2$, Fv, dsFv, dAb, scFv, and a single chain binding polypeptide.

In some embodiments, the present disclosure provides exemplary mouse monoclonal antibody HAb18GC2 (also referred as 6H8), the chimeric antibody thereof (i.e., c6H8), and the humanized antibodies HP6H8-1, HP6H8-2, HP6H8-3.

The mouse monoclonal antibody HAb18GC2 has a heavy chain variable region of SEQ ID NO: 31, light chain variable region of SEQ ID NO: 29. The chimeric antibody c6H8 comprises a human constant region of IgG1 isotype fused to the above-stated mouse variable region.

In some embodiments, the humanized anti-BASIGIN antibody is selected from a group consisting of HP61-18-1, HP6H8-2 and HP6H8-3, which have heavy chain variable region of SEQ ID NO: 3, 5 and 7 respectively (corresponding to encoding DNA sequences SEQ ID NO: 4, 6 and 8 respectively) and light chain variable region of SEQ ID NO. 16, 18 and 20 respectively (corresponding to encoding DNA sequences SEQ ID NO. 17, 19 and 21 respectively).

Method of Producing the Humanized Antibody or Antigen Binding Fragment

In some embodiments, the humanized anti-BASIGIN antibody or the antigen binding fragments thereof are prepared using recombinant methods. The recombinant process of producing the humanized anti-BASIGIN antibody or the antigen binding fragments thereof includes:

1) Immunizing a suitable non-human animal with human BASIGIN protein or hBASIGIN producing cells. The animal can be mouse, rat, sheep, goat, rabbit, or guinea pig Generating antibody producing hybridoma using the spleen or the lymph node from the non-human animal, or gathering B cells of the immunized non-human animal and measuring the non-human monoclonal anti-BASIGIN antibodies titer. Isolating and sequencing DNA encoding the monoclonal antibody by using conventional procedures (e.g., by using oligonucleotide probes that are capable of binding specifically to genes encoding the heavy and light chains of the antibody).

2) Cloning the polynucleotides encoding the non-human monoclonal anti-BASIGIN antibodies with suitable titer from the generated hybridoma or gathered B cell clones. Analyzing the sequence of the polypeptides encoded by the polynucleotides to identify the CDR boundaries for the non-human monoclonal antibodies.

3) Obtaining a recombinant gene of a humanized antibody or antigen binding fragment thereof by grafting the non-human derived antibody CDR genes into a human immunoglobulin gene, so that the variable region framework and constant regions are, if present, entirely or substantially from human immunoglobulin sequences.

4) Optionally incorporating the recombinant gene into a suitable vector, and introducing the vector or the recombinant gene into host cells to produce the humanized antibody or antigen fragment thereof provided herein.

The antibody and the antigen binding fragments thereof provided herein can be obtained in a substantially pure and homogeneous form by culturing the host cells, followed by separation and purification of the host cells or the culture liquid (e.g., supernatant). For the separation and purification of the antibody or the antigen binding fragments thereof, any conventional method of polypeptide purification can be employed.

Isolated Nucleic Acid Sequence

In one aspect, the present disclosure provides an isolated nucleic acid sequence encoding the humanized anti-BASIGIN antibody or antigen binding fragment thereof provided herein.

An "isolated" substance is a substance which is altered by the hand of man from its natural state, for example a naturally occurred substance removed from its original environment can be referred as an isolated substance. An "isolated" nucleic acid is a nucleic acid molecule that is substantially free of other nucleic acid molecules, and is not associated with naturally occurring components that accompany the nucleic acid in the native state. An "isolated nucleic acid sequence" refers to the sequence of an isolated nucleic acid molecule.

In some embodiments, the isolated nucleic acid sequences comprise one or more nucleotide sequences encoding the CDR sequences provided in the present disclosure. In some embodiments, the isolated nucleic acid sequence comprises a nucleotide sequence of SEQ ID NO:4, SEQ ID NO:6 or SEQ ID NO:8, or a homologue sequence thereof. In some embodiments, the isolated nucleic acid sequence comprises a nucleotide sequence of SEQ ID NO:17, SEQ ID NO:19 or SEQ ID NO:21, or a homologue sequence thereof.

As used herein, "homologue" and "homologous" are used interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

Percent (%) "sequence identity" with respect to nucleic acid sequence (or amino acid sequence) is defined as the percentage of nucleic acid (or amino acid) residues in a candidate sequence that are identical to the nucleic acid (or amino acid) residues in a reference sequence, after aligning the sequences and, if necessary, introducing gaps, to achieve the maximum correspondence. Alignment for purposes of determining percent nucleic acid (or amino acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215.403-410 (1990), Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment such as, for example, by selecting a suitable algorithm.

Vector

In another aspect, the present disclosure also provides a vector comprising the isolated nucleic acid sequence encoding the humanized anti-BASIGIN antibody or antigen binding fragment thereof.

The term "vector" as used herein, refers to a nucleic acid vehicle capable of transforming or transfecting cells and allowing gene expression in cells. A vector can be an expression vector or a cloning vector. The present disclosure provides vectors (e.g., expression vectors) containing the nucleic acid sequence provided herein encoding the antibody or antigen binding fragment thereof, at least one promoter (e.g., SV40, CMV, EF-1α) operably linked to the nucleic acid sequence, and at least one selection marker. The expression vectors of the present disclosure can be viral vectors, plasmids, phages and cosmids. Examples include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBl, p15TV-L, pPro18, pTD, pRS10, pLexA, pACT2.2, pCMV-SCRIPT.RTM., pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Host Cell

In another aspect, the present disclosure provides a host cell comprising a vector provided herein.

The "host cell" as used herein refers to a cell into which an exogenous nucleic acid and/or a vector has been introduced to express one or more exogenous proteins. The term "host cell" intends to refer to both the particular subject cell and the progeny thereof. A host cell can be a prokaryote, a eukaryote, a plant cell, an animal cell or a hybridoma Different host cells may have different characteristics and mechanisms for post-translational processing and modification of proteins and gene products, therefore suitable cell lines can be chosen as host cells to ensure the correct modification and processing (such as primary transcript, glycosylation, and phosphorylation) of the humanized anti-BASIGIN antibody or antigen binding fragment expressed. In some embodiments, the host cells are mammalian cells.

Examples of useful mammalian host cell lines are monkey kidney CV1 line transformed by SV40 (e.g., COS-7); human embryonic kidney line (e.g., 293 or 293T cells subcloned for growth in suspension culture), baby hamster kidney cells (BHK, ATCC CCL 10); Chinese hamster ovary cells (e.g., CHO/-DHFR, CHO/-GS, Urlaub et al., Proc. Natl. Acad. Sci. USA 77:116 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 141); human lung cells (W138, ATCC CCL 75); human hepatocellular carcinoma cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; PC12; mouse embryo fibroblast cell line (3T3); NS0 myeloma cells (a murine myeloma cell line that does not endogenously produce any functional immunoglobulin chains). In some embodiments, the host cells are CHO cells.

Host cells transformed with the above-described vectors or recombinant genes can be cultured in conventional nutrient media, or conventional nutrient media modified as appropriate for inducing promoters, selecting transformants, or amplifying the genes encoding the desired sequences. In some embodiments, the host cells may be co-transformed with a second polynucleotide encoding a different fragment of the antibody. In some embodiments, host cells can contain the exogenous nucleic acid but do not express a protein encoded by the exogenous nucleic acid at a desired level unless a regulatory agent is introduced into the cells or a regulatory sequence is introduced into the cells so that it is operably linked with the nucleic acid. In some embodiments, the host cells containing the transformed vectors can transiently express the anti-BASIGIN antibody.

Pharmaceutical Composition

In one aspect, the present disclosure provides a pharmaceutical composition comprises one or more humanized anti-BASIGIN antibody or antigen binding fragment thereof provided herein.

The pharmaceutical compositions provided herein can be in any conventional form known in the art, including but are not limited to, a liquid solution, suspension, emulsion, pill, capsule, tablet, sustained release formulation or powder. In some embodiments, the pharmaceutical compositions are formulated into an injectable composition. Examples of the injectable composition include sterile solutions ready for injection; sterile suspensions ready for injection, sterile emulsions ready for injection; sterile dry soluble products, such as lyophilized powders, ready to be reconstituted in a solvent just prior to use and such like. A lyophilized powder can be stored under appropriate conditions such as at about 4° C. to room temperature. The solutions useful for reconstitution may be either aqueous or non-aqueous. In some embodiments, unit-dose injectable composition are pre-packaged in an ampoule, a vial or a syringe with a needle. In some embodiments, multiple-dose injectable composition are pre-packaged in an ampoule or a vial.

In some embodiments, the pharmaceutical composition further comprises a pharmaceutically acceptable carrier.

The term "pharmaceutically acceptable" as used herein means that the designated carrier is generally chemically and/or physically compatible with the other ingredients comprised in the pharmaceutical composition, and within the scope of sound medical judgment, suitable for use in vivo in the recipient subject (e.g., human beings and animals) without excessive toxicity, irritation, allergic response, or other problem or complication, commensurate with a reasonable benefit/risk ratio.

The "pharmaceutical acceptable carriers" may include, for example, pharmaceutically acceptable aqueous, non-aqueous or solid vehicles, antimicrobial agents, isotonic agents, buffers, pH regulator, suspending/dispersing agents, sequestering or chelating agents, diluents, adjuvants, excipients, or non-toxic auxiliary substances, other components known in the art, or any combinations thereof, which can facilitate storage and administration of the active ingredients to a subject. Pharmaceutically acceptable carriers that can be employed in the present disclosure includes those generally known in the art, such as those described in "Remington Pharmaceutical Sciences" Mack Pub. Co., New Jersey (1991), which is incorporated herein by reference.

To further illustrate, pharmaceutical acceptable carriers may include, for example, sterile water, sodium chloride, dextrose, lactose, fructose, glucose, trehalose, sucrose, sorbitol, mannitol, xylitol, ethyl alcohol, polyethylene glycol, propylene glycol, phenol, cresol, benzyl alcohol, chlorobutanol, glycerol, proline, histidine, arginine, hydrochloric acid, acetic acid, citric acid, lactic acid, succinic acid, ascorbic acid, acetate, citrates, succinic acid citrate, phosphate, sorbitate, sucrose phosphates, sodium succinate, sodium citrate, ethanol sodium acetate, sodium hydroxide, methyl and propyl p-hydroxybenzoic acid esters, thimerosal, benzalkonium chloride, benzethonium chloride, sorbitan monolaurate, triethanolamine oleate, cyclodextrin, TWEEN®20 (polysorbate 20), TWEEN®80 (polysorbate 80), corn syrup, glycerin, sodium bisulfate, procaine hydrochloride, Poloxam, sodium carboxymethylcelluose, hydroxypropyl methylcellulose, polyvinyl pyrrolidone, EDTA, EGTA or other suitable agent.

In some embodiments, the pharmaceutical composition comprises humanized anti-BASIGIN antibody or antigen binding fragment thereof provided herein, and one or more other therapeutic agent. In some embodiments, the other therapeutic agent is an agent used in a radiation therapy, chemotherapy, targeted therapy, gene therapy, immunotherapy, hormonal therapy, angiogenesis inhibition, palliative care, surgery, antimalarial drug or the combination thereof.

Kits

The present disclosure provides kits comprising the anti-BASIGIN antibodies or the antigen binding fragments thereof provided herein. In some embodiments, the kits are useful for detecting the presence or the level of BASIGIN in a biological sample. The biological sample can be cells or tissues.

In some embodiments, the anti-BASIGIN antibody or the antigen binding fragment thereof contained in the kit is conjugated with a detectable label (for example, fluorescent, radioactive or enzymatic label). In some other embodiments, the kit comprises an unlabeled anti-BASIGIN antibody or antigen binding fragments thereof and further comprises a secondary labeled antibody which is capable of binding to the unlabeled anti-BASIGIN antibody. The kit may further include means of detecting a label. The kit may comprise additional reagents and buffers used for the performance of a particular method. The kit may further comprise an instruction of use, and a package that separates each of the components in the kit. In some embodiments, the kit comprises an immunoassay for detecting the BASIGIN antibody.

In some embodiments, the kit is provided for detecting BASIGIN protein level. In some embodiments, the kit is used for predicting, diagnosing, preventing or treating BASIGIN associated conditions.

Method of Treatment

In one aspect, the present disclosure provides a method of treating a BASIGIN related condition in a subject, which comprises administering an effective amount of the pharmaceutical composition provided herein to the subject.

In another aspect, the present disclosure provides use of the humanized anti-BASIGIN antibody or antigen binding fragment thereof provided herein in the manufacture of a medicament for treating a BASIGIN related condition in a subject.

In another aspect, the present disclosure provides the humanized anti-BASIGIN antibody or antigen binding fragment thereof of the present disclosure useful for treating a BASIGIN related condition in a subject.

The term "subject" as used herein refers to an animal. Typically, the animal is a mammal, particular examples include primates (e.g., humans), dogs, cats, horses, cows, pigs, and sheep. In some embodiments, the subject is human.

A "BASIGIN related condition" as used herein refers to any condition that is caused by, exacerbated by, or otherwise linked to increased or decreased expression or activities of BASIGIN (e.g., a human BASIGIN). In some embodiments, the BASIGIN related condition is cancer, inflammatory disease or infectious disease.

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer include but are not limited to, non-small cell lung cancer (squamous/nonsquamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma, classical Hodgkin lymphoma (CHL), primary mediastinal large B-cell lymphoma, T-cell/histiocyte-rich B-cell lymphoma, acute lymphocytic leukemia, acute myelocytic leukemia, acute myelogenous leukemia, chronic myelocytic (granulocytic) leukemia, chronic myelogenous leukemia, chronic lymphocytic leukemia, polycythemia vera, mast cell derived tumors, EBV-positive and-negative PTLD, and diffuse large B-cell lymphoma (DLBCL), plasmablastic lymphoma, extranodal NK/T-cell lymphoma, nasopharyngeal carcinoma, HHV8-associated primary effusion lymphoma, non-Hodgkin's lymphoma, multiple myeloma, Waldenstrom's macroglobulinemia, heavy chain disease, myelodysplastic syndrome, hairy cell leukemia and myelodysplasia, primary CNS lymphoma, spinal axis tumor, brain stem glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma. In some embodiments, the cancer is metastatic, especially BASIGIN expressing metastatic cancer.

In some embodiments, the BASIGIN associated conditions are inflammatory diseases such as systemic lupus erythematosus (SLE), intestinal mucosal inflammation, wasting disease associated with colitis, multiple sclerosis, viral infections, rheumatoid arthritis, osteoarthritis, Cohn's disease, and inflammatory bowel disease, psoriasis, systemic scleroderma, autoimmune diabetes and the like.

In some embodiments, the BASIGIN associated conditions are infectious disease such as fungus infection, parasite/protozoan infection or chronic viral infection, for example, malaria, coccidioiodmycosis immitis, histoplasmosis, onychomycosis, aspergilosis, blastomycosis, candidiasis albicans, paracoccidioiomycosis, microsporidiosis, Acanthamoeba keratitis, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, Trichuriasis, Trypanosomiasis, helminth infection, infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, human immunodeficiency virus I, human immunodeficiency virus II, Kaposi West sarcoma associated herpes virus epidemics, thin ring virus (Torquetenovirus), human T lymphotrophic viruse I, human T lymphotrophic viruse II, varicella zoster, JC virus or BK virus. In some embodiments, the condition is malaria.

"Treating", "treatment" or "therapy" of a condition as used herein can be used interchangeably, and includes therapeutic treatment, prophylactic or preventative measures such as preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "therapeutically effective amount" as used herein refers to the dosage or concentration of a drug effective to treat a disease or condition associated with human BASIGIN. For example, with regard to the use of the humanized anti-BASIGIN antibody or antigen binding fragments disclosed herein to treat cancer, a therapeutically effective amount is the dosage or concentration of the antibody or antigen binding fragment capable of reducing the tumor volume, inhibiting growth or proliferation of cancer cells, inhibiting or slowing tumor growth or cancer cell infiltration into other organs, inhibiting or slowing cancer cell metastasis, ameliorating any symptom associated with cancer, preventing or delaying the development of cancer, or some combination thereof. Or, with regard to the use of the humanized anti-BASIGIN antibody or antigen binding fragments disclosed herein to treat malaria, therapeutically effective amount is the dosage or concentration of the antibody or antigen binding fragment capable of inhibiting infection or proliferation of the plasmodium, ameliorating any symptom associated with a malaria condition, preventing or delaying the development of a malaria condition, or some combination thereof.

The therapeutically effective amount (when used alone or in combination with other agents such as chemotherapeutic agents) of humanized anti-BASIGIN antibody or antigen binding fragment as provided herein will depend on various factors known in the art, for example, type of disease to be treated, the type of antibody, body weight, age, past medical history, present medications, state of health of the subject, immune condition and potential for cross-reaction, allergies, sensitivities and adverse side-effects, as well as the administration route and the type, the severity and development of the disease and the discretion of the attending physician or veterinarian. In some embodiments, an humanized anti-BASIGIN antibody or antigen binding fragment as provided herein may be administered at a therapeutically effective dosage of about 0.01 mg/kg to about 100 mg/kg one or more times per day (e.g., about 0.01 mg/kg, about 0.3 mg/kg, about 0.5 mg/kg, about 1 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg one or more times per day). In some embodiments, the humanized anti-BASIGIN antibody or antigen binding fragment is administered at a dosage of about 50 mg/kg or less, and in some embodiment the dosage is 20 mg/kg or less, 10 mg/kg or less, 3 mg/kg or less, 1 mg/kg or less, 0.3 mg/kg or less, or 0.1 mg/kg or less. In some embodiments, the administration dosage may change over the course of treatment. For example, in some embodiments the initial administration dosage may be higher than the subsequent administration dosages. In some embodiments, the administration dosage may vary over the course of treatment depending on the reaction of the subject.

Dosage regimens may be adjusted to provide the optimum desired response (e.g., a therapeutic response). In some embodiments, the humanized anti-BASIGIN antibody or antigen binding fragment as provided herein is administered to the subject at one time or over a series of treatments. In some embodiments, the humanized anti-BASIGIN antibody or antigen binding fragment as provided herein is administered to the subject by one or more separate administrations, or by continuous infusion depending on the type and severity of the disease. Guidance can be found in, for example, U.S. Pat. Nos. 4,657,760; 5,206,344; 5,225,212.

The humanized anti-BASIGIN antibodies and antigen binding fragments disclosed herein may be administered by any route known in the art such as, for example, parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the humanized anti-BASIGIN antibodies and antigen binding fragments disclosed herein may be administered in a controlled-release manner. A controlled-release parenteral preparations can be made as implants, oily injections or particulate systems (e.g., microspheres, microparticles, microcapsules, nanocapsules, nanospheres, and nanoparticles) (see Banga, A. J., Therapeutic Peptides and Proteins: Formulation, Processing, and Delivery Systems, Technomic Publishing Company, Inc., Lancaster, Pa., (1995), Kreuter, J., Colloidal Drug Delivery Systems, J. Kreuter, ed., Marcel Dekker, Inc., New York, N.Y., pp. 219-31 (1994); Tice & Tabibi, Treatise on Controlled Drug Delivery, A. Kydonieus, ed., Marcel Dekker, Inc. New York, N.Y., pp. 315-339, (1992)). In some embodiments, the humanized anti-BASIGIN antibodies and antigen binding fragments provided herein may be administered in degradable or nondegradable polymeric matrices (see Langer, Accounts Chem. Res. 26:537-51, 1993).

Unless defined otherwise, all technical and scientific terms used herein have the same meaning as commonly understood by one of ordinary skill in the art to which this invention belongs.

As used herein, the singular forms "a", "an" and "the" are intended to include the plural forms as well, unless the context clearly indicates otherwise. It will be further understood that the terms "comprises", "comprising", "includes", "including", "have" and/or "having" if used herein, specify the presence of stated features, steps, operations, elements and/or components, but do not preclude the presence or addition of one or more other features, steps, operations, elements, components and/or groups thereof. As used herein, the term "about," when used in reference to a particular recited numerical value, means that the value may vary from the recited value by no more than 10%.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

EXAMPLES

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Construction of the Phage Display Vector

The hybridoma cell line HAb18GC2 was generated and deposited in China Center for Type Culture Collection in 2006, with the accession number of CCTCC-C200636. Detailed information about the cell line, the antibody produced by the cell line and the preparation method are described in Chinese patent ZL200710007452.2, which is incorporated herein by reference in its entirety.

Total RNA was extracted from hybridoma cell HAb18GC2 by using the Total RNA Extraction Kit (Omega bio-tek) according to the manual of the kit. The integrity of the extracted total RNA was analysed by agarose gel electrophoresis.

cDNA was prepared by taking 1 µg of the total RNA, synthesizing the cDNA first strand according to the manual of the reverse transcription kit PrimeScript RT reagent Kit (TaKaRa) and was stored at −20° C. for further experimentations.

The VH gene fragments and VL gene fragments were amplified from cDNA template by using the VH and VL gene specific primer sets, respectively, in a PCR reaction. Phusion® High-Fidelity DNA Polymerase (NEB) was used in the PCR, and the reaction mix is prepared according to the manual of NEB. PCR reaction condition is set as follows: 94° C., 5 min; (94° C., 15 s, 54° C., 30 s, 72° C., 1 min)×35 cycles, 72° C., 10 min. The size of the amplified fragments were determined in 1% agarose gel electrophoresis.

Linker sequence and its reverse complementary sequence were introduced to the 3' end of the VH gene fragment and the 5' end of the VL gene fragment, respectively, via primers (VH reverse linker-R1: SEQ ID NO: 34, CAAAGTTG-GAAATAAAAGCGGCCGCAGAACAAAA; VL linker-F1: SEQ ID NO: 35, TTTTGTTCTGCGGCCGCTTTTAT-TTCCAACTTTG) in a further PCR reaction.

The VH gene fragment and VL gene fragment with the linker sequence or the reverse complementary sequence of the linker sequence were mixed 1:1 (mol/mol) and scFv gene is amplified by using an overlap-PCR method. The reaction system was prepared as follows: 1 pmol VH gene fragment, 1 pmol VL gene fragment, 100 pmol pFL-6H8-F1 primer (SEQ ID NO: 33 CCCAGCCGGC-CATGGCCGAAGTGAAGCTTGAGGAGTCT), 100 pmol pFL-6H8-R2 primer (SEQ ID NO: 36 TTTTGTTCTGCGGCCGCTTTTATTTCCAACTTTG), 10 µl 10× PCR buffer. PCR reaction condition was set as follows: 95° C., 5 min; (95° C., 15 s, 56° C., 30 s, 72° C., 1 min)×35 cycles, 72° C., 10 min. The size of the amplified fragment was determined in 1% agarose gel electrophoresis.

The band at expected size was cut out, and recovered by using the DNA fragment purification kit (Omega bio-tek) to obtain a scFv gene fragment containing the restriction sites of Nco I and Not I.

The scFv gene fragment containing the cleavage site Nco I and Not I and the vector plasmid pGEM-T vector (Promega) were measured with an ultraviolet spectrophotometer, and then subjected to restriction enzyme digestion.

The reaction was set as follows: mixed 3 µg of recovered scFv gene fragment or 3 µg of pGEM-T vector, 1 µl Nco I-HF, 1 µl Not I-HF restriction endonucleases (NEB), 5 µl 10× CUTSMART® Buffer, and added water to 50 µl. The digestion reaction mix was incubated at 37° C. for 1 h. The size of the obtained products were determined in 1% agarose gel electrophoresis, and bands at expected size were cut out, and recovered by using the DNA fragment purification kit (Omega bio-tek) to obtain a digested scFv gene fragment and digested pGEM-T vector.

After digestion, the recovered scFv gene fragment and pGEM-T vector were ligated. The ligation reaction mix was set as follows: 0.7 µg digested scFv gene fragment, 1.4 µg digested pGEM-T vector, 40 U T4 ligase, 40 µl 5× ligation buffer. The ligation reaction mix was incubated at 16° C. overnight. TG1 competent cells were transformed with ligation product, then spreaded on LB agar plates and incubated at 37° C. overnight. Separate colonies were picked and screened for positive clones with the universal primer for vector. The positive clones were then sequenced for correct insert, and those proved to contain the correct insert (named as recombinant plasmid pFL-6H8) were stored at −40C for further use. The recombinant plasmid pFL-6H8 contains scFv gene with the complete heavy chain and light chain variable region sequences.

Example 2: Determination for CDRs and FRs of the Mouse Monoclonal Antibody 6H8

The CDRs in the light chain and heavy chain variable region of the mouse monoclonal anti-hBASIGIN antibody 6H8 (also known as HAb18GC2, see in Chinese patent: ZL200710007452.2) were determined according to the Kabat database. The amino acid sequences of the three light chain CDRs are shown in SEQ ID NO: 22, SEQ ID NO: 23 and SEQ ID NO: 24 in the Sequence Listing, respectively. The amino acid sequences of the three heavy chain CDRs are shown in SEQ ID NO: 9, SEQ ID NO: 10 and SEQ ID NO: 11 in the Sequence Listing, respectively.

Figure 1:
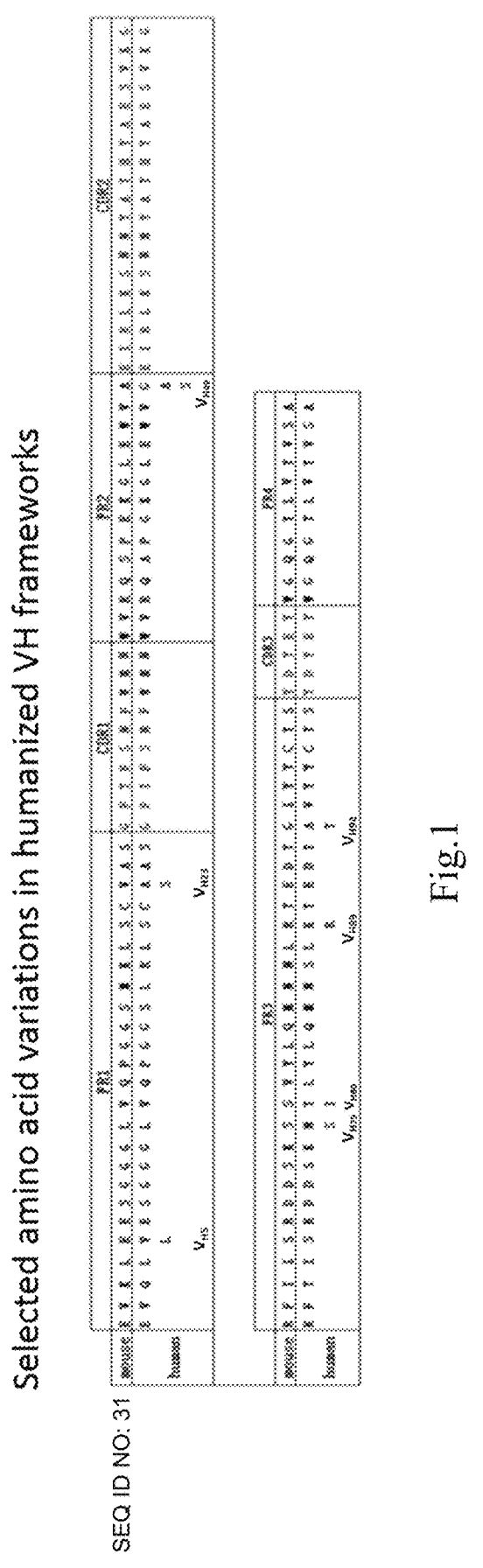
Figure 2:
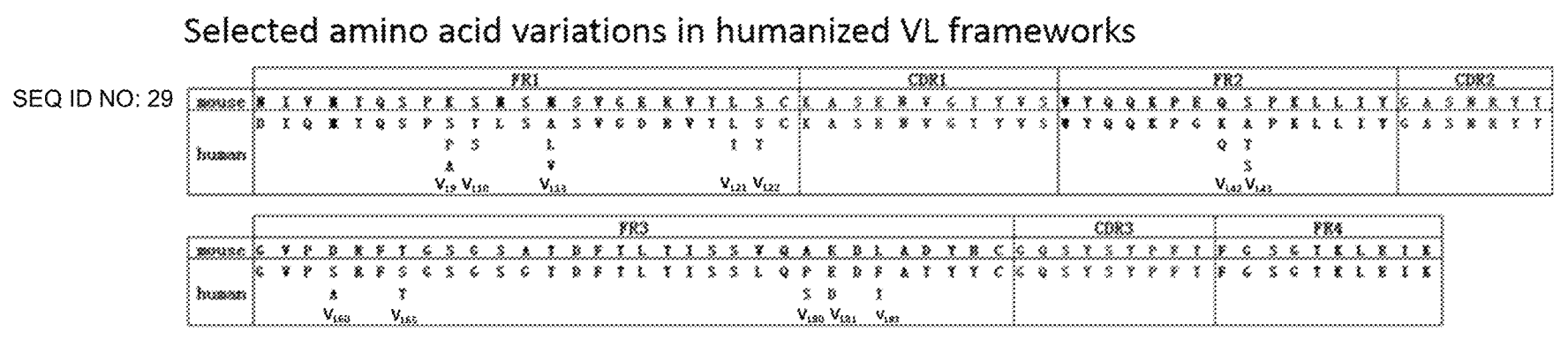

Example 3: Selection of Appropriate Human Immunoglobulin Framework Sequences The human FR sequences obtained from Kabat database were grafted with the aforementioned CDRs for humanization of the antibody and the grafted antibody variable regions were screened for homology and structures. A computer software named Discovery Vision (VIOVIA, version 3.5) was used to analyze the molecular structure of the antibody before and after humanization through the molecular modeling, homology modeling and mechanics optimization, and to verify possible alterations in the human FRs to ensure that the replaced FRs does not change the overall skeleton structure of VH and VL, in particular, does not destroy the β-strand secondary structure of the mouse monoclonal antibody thereby maintains or improves the affinity of the original mouse antibody. The selected human heavy/light chain variable FR sequences with possible variations at specific sites were listed in line with the mouse FR sequences in FIG. 1 and FIG. 2 of the present disclosure.

Example 4: Construction and Screening of Phage Display Humanized Anti-hBASIGIN Antibody Library Based on the sequences of CDRs determined in example 2 and FR sequences verified in example 3, the corresponding nucleotide sequence encoding the ScFv fragment of the humanized antibody was obtained by using commonly used codons in mammalian cells. The encoding gene was obtained by overlap-PCR method, then cloned into the cloning vector and amplified, and the positive clones were subject to sequencing analysis. Humanization of the FRs was performed by introducing alterations and variations at specific amino acid sites in the coding sequence of the heavy/light chain FRs by primers. Detailed protocol was described below.

Material

Mouse derived scFv fragment from example 1 was used as template. Following primers were used for amplification of the humanized heavy chain variable region (hVH) and humanized light chain variable region (hVL).

hVH forward primers include:
1) 6H8-L1-F1: SEQ ID NO: 37

CAGCCGGCCATGGCCGAAGTGCAGCTTGTGGAGTCTG 2) 6H8-L1-F2: SEQ ID NO: 38 (6H8-L1-F2 represents a mixture of primers, wherein R=G or A, S=G or C)

CGCCAGGCTCCAGGGAAGGGGCTTGAGTGGGTTRSCGAAATT

AGATTGAAATC 3) 6H8-L1-F3: SEQ ID NO: 39 (6H8-L1-F3 represents a mixture of primers, wherein R=G or A)

CAGATGAACTCCTTAARGACTGAAGACACTGCCGTGTATTACTGT

ACCAG hVH reverse primers include:
1) 6H8-L1-R1: SEQ ID NO: 40 (6118-L1-R1 represents a mixture of primers, wherein M:=A or C, Y:=T or C)

GAAAGTGAATCCAGAGGCGGMACAGGAGAGCYTCAGGGATCCT

CCAGG 2) 6H8-L1_R2: SEQ ID NO: 41

CCCTGGAGCCTGGCGGACCCAGTTCATCCAGAAGTTACTGAAAG

TGAATCCAG 3) 6H8-L1-R3: SEQ ID NO: 42 (6H8-L1-R3 represents a mixture of primers, wherein R=G or A, K=G or T)

TAAGGAGTTCATCTGCAGGTACAGGRTGKTTTTGGAATCATCTCTTG 4) 6H8-L1-R4: SEQ ID NO: 43

GGGAGATTGGGTCATCTGAATGTCGCTAGCACCGCCAC 5) 6118-L1_R5. SEQ ID NO. 44 (61-18-L1_R5 represents a mixture of primers, wherein R=G or A, S=G or C, W=A or T, V=G or C or A)

GGTGACCCTGTCGCCCACTGAGRSGGACAGGGWGGVGGGAGATT

GGGTC hVL forward primers include:
1) 6H8-L1_F4: SEQ ID NO: 45 (6H8-L1_F4 represents a mixture of primers, wherein M=A or C, W=A or T)

GTGGGCGACAGGGTCACCMTCWCCTGCAAGGCCAGTGAG 2) 6H8-L1_F6: SEQ ID NO: 46 (6H8-L1_F6 represents a mixture of primers, wherein Y=T or C, S=G or C, W=A or T)

TCAGCAGTCTGCAGYCCGASGACWTCGCAACCTATTACTGTGGA

CAGAGTTAC 3) 6H8-L1_F5: SEQ ID NO:

CCGGCAGTGGATCTGGCACAGATTTCACTCTGACCATCAGCAGT

CTGCAG hVL reverse primers include:
1) 6H8-L1_R6: SEQ ID NO: 48 (6H8-L1_R6 represents a mixture of primers, wherein H=A or C or T, K=G or T)

GTTGGATGCCCCGTATATCAGCAGTTTAGGGGHCTKGCCTGGTT

TCTGTTG 2) 6H8-L1_R8: SEQ ID NO: 49

TTTGTTCTGCGGCCGCTTTTATTTCCAACTTTGTCCC 3) 61-18-L1_R7: SEQ ID NO 50 (Primer 6H8-L1_R7 is a mixture of primers, wherein W=A or T, M=A or C)

AGATCCACTGCCGGWGAAGCGGGMGGGGACCCCAGTGTACCGG

TTGGATGCCCC

Method and Results

Target fragments were amplified by following the amplification scheme as set below:

1$^{st}$ step amplification five pairs of primers (6H8-L11-F1+6H8-L1-R1, 6H8-L1-F2+6H8-L1-R3, 6H8-L1-F3+6H8-L1-R4, 6H8-L1_F4+6H8-L1_R6, 6H8-L_F6+6H8-L1 R8) were used to amplify five 14 step fragments from pFL-6H8 vector obtained in Example 1. PCR reaction condition was set as follows: 95° C., 3 min; (95° C., 30 s, 55° C., 30 s, 72° C., 40 s)×40 cycles: 72° C., 10 min. After the PCR, the size of the amplified fragments were determined in 1% agarose gel electrophoresis and then ligated into the pMD18-T vector (TaKaRa). The ligation products were transformed into competent cells, and clones were selected and screened for correct insertion. Based on the sequencing results, fragments with the correct sequences were named 6H8-L1-1, 6H8-L1-2, 6H8-L1-3, 6H8-L1-4 and 6H8-L1-5, respectively.

2$^{nd}$ step amplification: the five 1$^{st}$ step fragments obtained above (6H8-L1-1, 6H8-L1-2, 61-18-L1-3, 6H8-L1-4 and 6H8-L1-5) were used as templates, and four pairs of primers (6H8-L1-F1+6H8-L1_R2, 6H8-L1-F2+6H8-L1 R5, 6H8-L1_F4+6H8-L1_R7,6H8-L1_F5+6H8-L1 R8) were used to amplify the 2$^{nd}$ step fragments. PCR reaction condition was the same as in the 1$^{st}$ step amplification After the PCR, the PCR products were purified through 1% agarose gel electrophoresis, and ligated into pMD18-T vector (TaKaRa) and transformed into competent cells. The positive clones were selected and screened for correct insertion. Based on the sequencing results, fragments with the correct sequences were named 6H8-L1-6, 6H8-L1-9, 6H8-L1-7 and 6H8-L1-8, respectively.

3$^{th}$ step amplification: following the same procedure as 1$^{st}$ step amplification, two 2$^{nd}$ step fragments obtained above (6H8-L1-6 and 6H8-L1-9) were used as templates, and a pair of primers (6H8-L1-F1+6H8-L1_R5) were used to obtain a 3$^{rd}$ step fragment (6H8-L1-10); two 2$^{nd}$ step fragments obtained above (6H8-L1-7 and 6H8-L1-8) were used as templates, and a pair of primers (6H8-L1_F4+6H8-L1_R8) were used to obtain a 3$^{rd}$ step fragment (61-18-L11-11).

4$^{th}$ step amplification following the same procedure as 1$^{st}$ step amplification, the 3$^{rd}$ step fragments obtained above (6H8-L1-10 and 61-18-L1-11) were used as templates, a pair of primers (6H8-L1-F1+6H8-L1_R8) were used to obtain a 4$^{th}$ step fragment (6H8-L1-12).

The 6H8-L1-12 fragment was digested with restriction enzymes NcoI-HF and NotI-HF (NEB), followed by separation through 1% agarose gel electrophoresis, and then the digested fragment was purified by Gel Extraction Kit (Omega bio-tek). The purified digested fragment was ligated with the phage vector pComb3Xss (including a c-myc fusion protein pre-engineered into the backbone of the phage vector) which is digested with the same set of restriction enzymes (i.e., NcoI-HF and NotI-HF) via T4 DNA ligase (TaKaRa). The ligation product was deionized and then transformed into TG1 competent cells via electroporation. The transformed TG1 cells were inoculated on LB plates for clone screening. The capacity of the 6H8-L1 antibody phage library was recorded, and the library was stored at −80° C. for further use.

Antigen specificity panning of the 6H8-L1 antibody phage library was carried out by solid-phase panning, with following steps:

The 6H8-L1 antibody phage library was revived in 60 ml of 2YT medium, and incubated in a shaker incubator at 37° C. until the OD600 of the culture reached 0.3-0.4. M13KO7 helper phage (Invitrogen) was added, and the culture was incubated for 30 min in a still incubator and incubated for 60 min in a shaker incubator at 37° C. The culture was centrifuged at 1500 rpm for 10 min, the supernatant was discarded, and the cells were re-suspended with 60 ml of 50 μg/ml kanamycin containing 2YT medium (without glucose). The re-suspended culture was incubated overnight in a shaker incubator at 30° C., centrifuged at 12,000 rpm for 10 min to precipitate the phage display library containing bacteria. The supernatant was transferred into a fresh centrifuge tube, aliquoted into 30 ml/tube lot, 7.5 ml of PEG/NaCl was added to each centrifuge tube, mixed well, placed on ice for 1 h, and centrifuged at 12000 rpm for 5 min, the supernatant was discarded, and the phages were re-suspended with 2.2 ml of solution containing PBS-5% BSA. The re-suspended phages were centrifuged at 12000 rpm for 5 min again to remove cell debris.

Human BASIGIN coated plates were used to conduct affinity panning for 5 rounds panning (binding-washing-amplifying), for each round of panning the coating concentration of the antigen was decreased gradually (1 μg/ml, 0.1 μg/ml, 0.01 μg/ml, 0.001 μg/ml, 0.0001 μg/ml). The panning experiment was terminated when the signal-to-noise ratio (S/N) was below 10. 768 clones were selected and the selected clones were cultured and induced to express the scFv antibodies which were used for ELISA analysis.

Example 5: ELISA and Sequencing Analyses

Human BASIGIN was diluted to 1 μg/ml with coating buffer (200 mM $Na_2CO_3$/$NaHCO_3$, pH 9.2), 50 μl of which was added to each well of 96-well plates and incubated overnight at 4° C. The coating solution in each well was discarded and the plates were washed with 1× PBS buffer for 3 times, blocked with 200 μl of blocking buffer (2% BSA/1× PBS buffer) per well at room temperature for 1 h, and then washed with 200 μl of 1×PBS buffer per well. The cell culture supernatant containing ScFv antibodies and negative control were added into individual wells of the plates, and incubated at room temperature for 2 h. The plates were then washed with 200 μl of 1× PBS buffer for 3 times. Anti-c-Myc Ab (HRP) as secondary antibody (Abcam Cat πab19312, 50 μl/well) that was diluted by blocking buffer (1:2500) was added into individual wells of the plates, and incubated at room temperature for 1 h. The plates were then washed with 200 μl of 1× PBS buffer for 6 times. TMB substrate solution (50 μl/well) was added to each well to react for 10 min, and the stopping solution (2 M HCl, 50 μl/well) was added to terminate the reaction. The absorbance at 450 nm was read in an ELISA plate reader. According to the results of ELISA, 123 clones of A450>2.0 were selected for sequencing analysis.

The DNA sequences results from the sequencing were evaluated for humanization degree with reference to the human immunoglobulin germline database and the website (bioinf.org.uk/abs/shab/). 26 scFV molecules with highest degree of humanization were selected for affinity sorting.

Example 6: Determination of scFv Binding Affinity by SPR

The affinity of the antibody was measured with ProteOn XPR36 (Bio-Rad) The GLC chip (Bio-Rad, 1765011) was activated with 0.04 M EDC+0.01 M sulfo-NHS (Bio-Rad). The human BASIGIN was diluted to 10 mM with 10 mM NaAc (pH 4.5) and then injected onto the chip at the rate of 30 μl/min to couple the antigen with the activated chip via amino groups. Finally, the chip were inactivated with 1 M ethanolamine-HCl (Bio-Rad), and when the chip was rotated for 90 degrees, it was washed with a buffer (PBS/0.005% Tween 20) until the baseline was stable. Five cell culture supernatants containing scFv antibody and one negative control were injected on six horizontal channels, respectively, at feeding rate of 30 μl/min. The time for binding was set as 60 s and the time for dissociation was set as 900 s. The data were analyzed using the Kinetic-Langmuir model.

SPR were used for real-time monitoring of the binding of human BASIGIN with the TG1 supernatant containing scFv antibodies. The association rate constant ($K_{on}$) of all screened antibodies were comparable, therefore the dissociation rate constant ($K_{off}$) was used for determine the binding affinity of the antibodies instead of $K_D$. The binding affinity of human BASIGIN with humanized scFv antibodies was pre-evaluated according to the $K_{off}$, and the results are shown in Table 1.

TABLE 1

SPR determination of scFv antibody affinity results

| Clone No. | $K_{off}$ (×10⁻⁵) | Clone No. | $K_{off}$ (×10⁻⁵) | Clone No. | $K_{off}$(×10⁻⁵) |
|---|---|---|---|---|---|
| 11131 | 8.9 | 11205 | 35 | 11189 | 5.2 |
| 11135 | 32 | 11210 | 32 | 11193 | 5.5 |
| 11143 | 10 | 11211 | 5.3 | 11195 | 5.3 |
| 11149 | 9.5 | 11214 | 5.2 | 11198 | 30 |
| 11156 | 36 | 11230 | 39 | 11120 | 23 |
| 11182 | 40 | 11232 | 30 | 11203 | 9.3 |
| 11187 | 6.4 | 11233 | 27 | 11246 | 41 |
| 11188 | 4.4 | 11242 | 3.4 | 11305 | 6.9 |
| 11204 | 14 | 11245 | 4.1 | mouse 6H8 | 11.4 |

Taking into consideration of other features, five humanized scFvs (i.e., 11188, 11214, 11242, 11245 and 11305) were selected from those with relatively lower $K_{off}$ values for constructing intact antibodies respectively.

Example 7: Construction of Intact Humanized Antibody

According to the results of the previous affinity sorting, five clones with the selected scFvs were inoculated overnight. The plasmids were extract from each overnight culture, and the sequences of which were confirmed by sequencing.

The following primers were used for amplification of the humanized heavy chain variable region (VH) and humanized light chain variable region (VL) for generating an intact humanized antibody:

VL forward primer: PCI-wbp229_F1, SEQ ID NO: 51

GCTCCCCGGGGCGCGCTGTGACATTCAGATGACCCAATC

VL reverse primer: pCI-6H8_R8, SEQ ID NO. 52

GGTGCAGCCACCGTACGTTTTATTTCCAACTTTGTCCCCGAG

VH forward primers include:
1) PCI-wbp229_F2: SEQ ID NO: 53

CTCTCCACAGGTGTACACTCCGAAGTGCAGCTTCTGGAGTC

2) PCI-wbp229_F3: SEQ ID NO: 54

CTCTCCACAGGTGTACACTCCGAAGTGCAGCTTGTGGAGTC 3) 6H8-L1_R2: SEQ ID NO: 55

CCCTGGAGCCTGGCGGACCCAGTTCATCCAGAAGTTACTGAAAG

TGAATCCAG 4) 6H8-L1_R5: SEQ ID NO: 56

GGTGACCCTGTCGCCCACTGAGRSGGACAGGGWGGVGGGAGATT

GGGTC

VH reverse primer: PCI-wbp229_R1, see SEQ ID NO: 57

GGGCCCTTGGTCGACGCTGCAGAGACAGTGACCAGAGTC

Target fragments were amplified by following the amplification scheme as set below:

Plasmid from 11188 was used as template, primer pairs (PCI-wbp229_F1+pCI-6H8_R8 and PCI-wbp229_F2+PCI-wbp229_R1) were used to amplify VL and VH regions for the intact humanized antibody WBP229-201.

Plasmid from 11214 was used as template, primer pairs (PCI-wbp229_F1+pCI-6H8_R8 and PCI-wbp229_F2+PCI-wbp229_R1) were used to amplify VL, and VH regions for the intact humanized antibody WBP229-202.

Plasmid from 11242 was used as template, primer pairs (PCI-wbp229_F1+pCI-6H8_R8 and PCI-wbp229_F3+PCI-wbp229_R1) were used to amplify VL and VH regions for the intact humanized antibody WBP229-203.

Plasmid from 11245 was used as template, primer pairs (PCI-wbp229_F1+pCI-6H8_R8 and PCI-wbp229_F2+PCI-wbp229_R1) were used to amplify VL and VH regions for the intact humanized antibody WBP229-204.

Plasmid from 11305 was used as template, primer pairs (PCI-wbp229_F1+pCI-6H8_R8 and PCI-wbp229_F3+PCI-wbp229_R1) were used to amplify VL and VH regions for the intact humanized antibody WBP229-205.

After the PCR, the amplified fragments were separated in 1% agarose gel electrophoresis, and bands at expected size were recovered and purified.

The purified VL/VH fragments were digested with NgoMIV and SnaBI, and the digested fragments were purified with DNA purification kit, and then ligated to the mammalian expression vector pCI-vector which included a (hIgG2 heavy chain constant region or human κ chain constant region) gene and which was digested with the same enzymes. The ligation products were transformed into TOP10 E. coli cells (Invitrogen), and the transformed cells were spreaded on LB agar plates with 100 μg/ml of ampicillin. Positive clones were then inoculated in LB liquid medium with 100 μg/ml of ampicillin, and after the clone were verified by sequencing, clone plasmids were extracted by using a Midi-Prep plasmid extraction kit (QIAGEN). The plasmids prepared were named pCI-WBP229-201L and pCI-WBP229-201H, pCI-WBP229-202L and pCI-WBP229-202H, pCI-WBP229-203L and pCI-WBP229-203H, pCI-WBP229-204L and pCI-WBP229-204H, pCI-WBP229-205L and pCI-WBP229-205H respectively, each of which contains a complete light chain gene or a complete heavy chain gene for producing an intact humanized antibody.

Example 8: Transient Transfection of Cells and Antibody Purification

HEK293 cells (1.0×10⁶ cells/ml) was co-transfected with a pair of plasmids containing one light chain gene and one corresponding heavy chain gene (e.g., pCI-WBP229-201 L/H~205L/H) by using FREESTYLE™ MAX Reagent from Invitrogen. The transfected cells were inoculated in a shaker incubator at 37° C. with 5% $CO_2$, and a rotation speed of 120 rpm. Culture supernatants were collected after 7 days post-transfection by centrifugation, and Protein A affinity chromatography columns were used to isolate and purify target antibodies from the supernatants. Three cultures with the highest humanized antibody production were selected, which were:

1) HP6H8-1 (corresponds to pCI-WBP229-205L/H) with amino acid sequence of heavy chain variable region of SEQ ID NO: 3, and amino acid sequence of light chain variable region of SEQ ID NO. 16.

2) HP6H8-2 (corresponds to pCI-WBP229-204l/H) with amino acid sequence of heavy chain variable region of SEQ ID NO. 5, and amino acid sequence of light chain variable region of SEQ ID NO: 18.

3) HP6H8-3 (corresponds to pCI-WBP229-203L/H) with amino acid sequence of heavy chain variable region of SEQ ID NO: 7, and amino acid sequence of light chain variable region of SEQ ID NO: 20.

Example 9: Determination of Binding Affinity of the Humanized Anti-hBASIGIN Antibodies 200 ng of human BASIGIN recombinant protein was coated in an ELISA plate and allowed to stand overnight at 4° C. The coated plate was blocked with 0.1% BSA at room temperature for 1 hour. Three antibodies obtained in example 8 along with the parental mouse monoclonal 6H8 and chimeric antibody c6H8 were each prepared into 5 solutions with gradient concentrations of 10, 100, 1,000, 10,000 and 100,000 ng/ml. 100 µl of each solution was added into individual wells and the plate was allowed to stand at room temperature for 1 hour. 100 µl of 1:4,000 diluted horseradish peroxidase-labeled goat anti-human light chain constant region as secondary antibody (Millipore) was added and allowed to stand at room temperature for 1 hour. The plates were then washed with 200 µl of 1× PBS buffer for 3 times, TMB substrate solution (50 µl/well) was added to each well to react for 10 min, and the stopping solution (2 M HCl, 50 µl/well) was added to terminate the reaction. The absorbance at 450 nm was read in an ELISA plate reader.

According to the result, the three humanized antibodies and the chimeric antibody c6H8 showed significantly higher affinity to human BASIGIN when compared with the parental mouse antibody 6H8 (FIG. 3).

The binding affinity of the three humanized antibodies, the mouse antibody 6H8 and the chimeric antibody c6H8 were also determined by SPR (for detailed steps, please refer to the description in example 6), data were shown in Table 2.

TABLE 2

SPR determination of the binding affinity of humanized antibodies

| Sample | $K_a$ (1/ms) | $K_d$ (1/s) | $K_D$ (M) | $R_{max}$ (RU) | Chi$^2$ (RU) |
|---|---|---|---|---|---|
| Mouse monoclonal 6H8 | 5.66E+04 | 6.64E−05 | 1.17E−09 | 175.08 | 3.20 |
| c6H8 | 1.28E+05 | 5.81E−05 | 4.52E−10 | 98.59 | 4.00 |
| HP6H8-3 | 5.31E+05 | 5.44E−05 | 1.02E−10 | 88.59 | 1.23 |

TABLE 2-continued

SPR determination of the binding affinity of humanized antibodies

| Sample | $K_a$ (1/ms) | $K_d$ (1/s) | $K_D$ (M) | $R_{max}$ (RU) | Chi$^2$ (RU) |
|---|---|---|---|---|---|
| HP6H8-2 | 6.18E+05 | 3.60E−05 | 5.83E−11 | 120.50 | 2.29 |
| HP6H8-1 | 5.48E+05 | 4.96E−05 | 9.05E−11 | 57.32 | 1.08 |

As shown in FIG. 3 and table 2, the binding affinity of the humanized antibodies were higher than that of the parental mouse antibody 6H8. The immunogenicity of the humanized antibodies in human are lower than that of the parental mouse antibody 6H8 and the stability of the humanized antibodies are better than that of the parental mouse antibody 6H8.

Example 10: Construction of Highly Efficient Humanized Anti-hBASIGIN Antibody Expression Vector and Screening of Stable Expression Cell Lines According to the results of example 9, gene sequence of HP6H8-1 was used for construction of highly efficient humanized antibody expression vector.

1. Construction of Light Chain Gene Expression Vector

Figure 4:
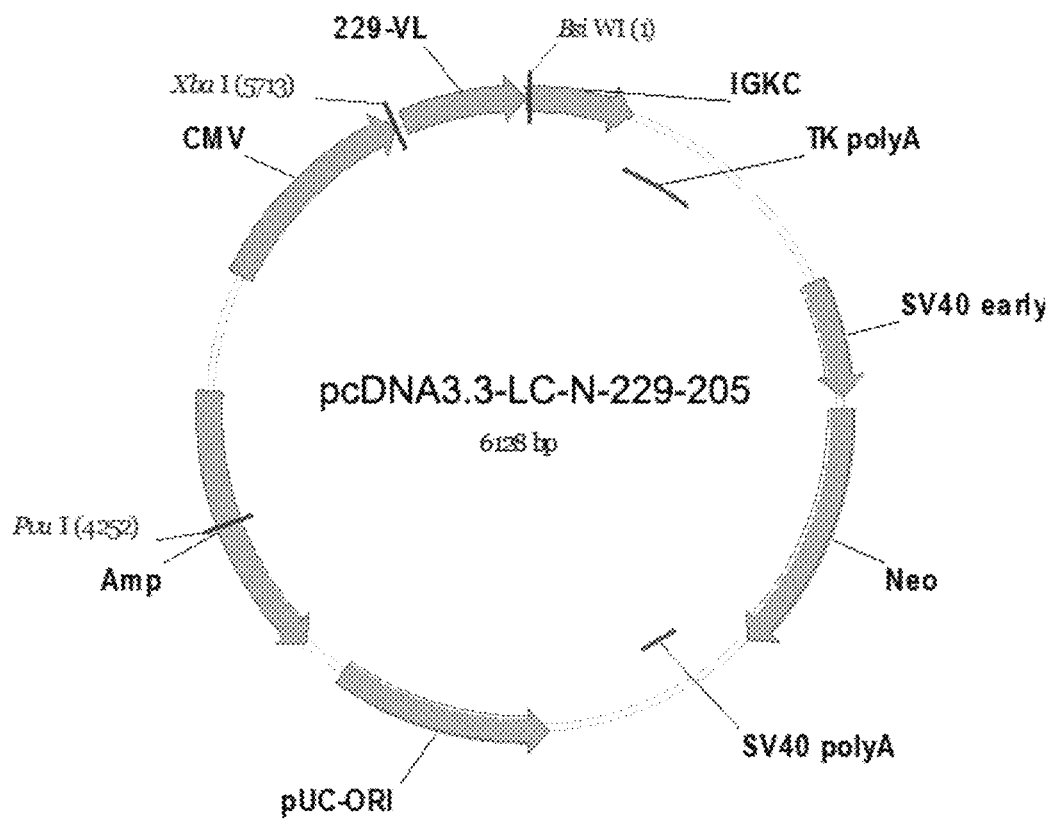
FIG. 4 is a schematic structure of the anti-BASIGIN antibody light chain gene expression vector pcDNA3.3-LC-N-229-205, the sequence encoding light chain variable region is inserted in between Xba I and Bsi WI sites of the pcDNA3.3 plasmid followed by the sequence encoding constant region of human kappa chain.

The gene sequence encoding the VL region of the HP6H8-1 was synthesized and added with restriction enzyme recognition sites of XbaI and BsiWI at 5' and 3' ends of the sequence, respectively. The synthesized molecule and the pcDNA3.3-LC-104new-M plasmid with light chain constant gene were digested with restriction enzymes XbaI and BsiWI. The digested products were separated in 1% agarose gel electrophoresis, and bands at expected size were recovered and purified. The purified fragments (a fragment of 416 bp derived from the synthetic molecule and a fragment of 5,712 bp derived from the pcDNA3.3-LC-104new-M plasmid) were ligated by using T4 ligase and the reaction mix was kept at 16° C. for 20 min. 10 µl out of 20 µl ligation solution was used to transform E. coli TOP10 competent cells (Invitrogen) After the transformed colonies were confirmed by PCR analysis, enzyme digestion analysis and sequencing, one correct mono-clone was inoculated overnight in 200 ml LB medium at 37° C. in a shaker incubator with 220 rpm. The plasmid was extracted and named pcDNA3.3-LC-N-229-205 (shown in FIG. 4).

2. Construction of Heavy Chain Gene Expression Vector

Figure 5:
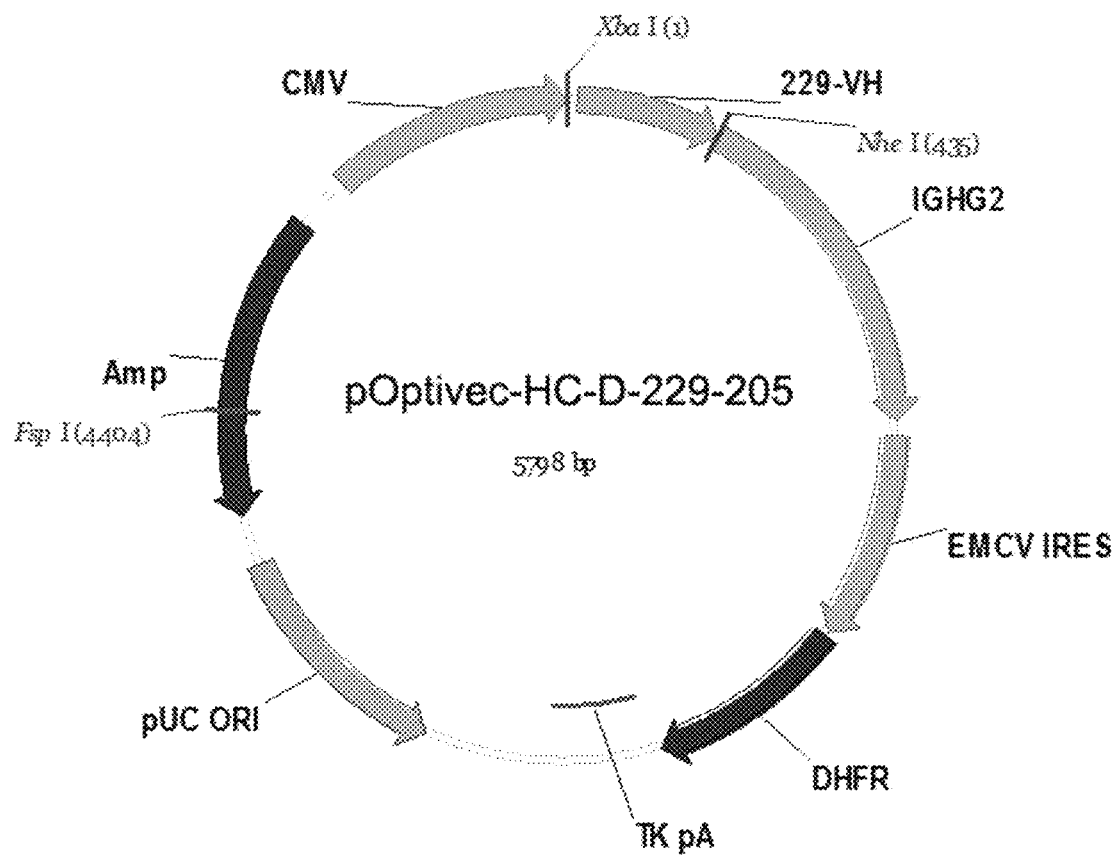
FIG. 5 is a schematic structure of the anti-BASIGIN antibody heavy chain gene expression vector pOptivec-HC-D-229-205, the sequence encoding heavy chain variable region is inserted in between Xba I and Nhe I sites of the pOptivec plasmid followed by sequence encoding constant region of human IgG2 heavy chain.

Similarly, the gene sequence encoding the VH region of the HP6H8-1 was synthesized and added with restriction enzyme recognition sites of XbaI and NheI at 5' and 3' ends of the sequence, respectively. The synthesized molecule and the pOptivec-HC-208-M plasmid with heavy chain constant gene were digested with restriction enzymes XbaI and NheI. The digested products were separated in 1% agarose gel electrophoresis, and bands at expected size were recovered and purified. The purified fragments (a fragment of 434 bp derived from the synthetic molecule and a fragment of 5,364 bp derived from the pOptivec-HC-208-M plasmid) were ligated by using T4 ligase and the reaction mix was kept at 16° C. for 20 min. 10 µl out of 20 µl ligation solution was used to transform E. coli TOP10 competent cells (Invitrogen). After the transformed colonies were confirmed by PCR analysis, enzyme digestion analysis and sequencing, one correct mono-clone was inoculated overnight in 200 ml LB medium at 37° C. in a shaker incubator with 220 rpm. The plasmid was extracted and named pOptivec-HC-D-229-205 (shown in FIG. 5).

3. Construction and Screening of CHO Stable Expression Cell Lines

Figure 6:
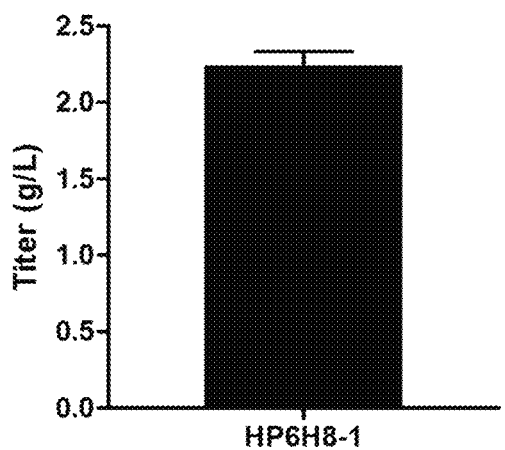
FIG. 6 shows the results of expression of HP6H8-1 antibody in a Chinese Hamster Ovary (CHO) cell line.

The humanized antibody light chain expression vector pcDNA3.3-LC-N-229-205 and the humanized antibody heavy chain expression vector pOptivec-HC-D-229-205 were transfected into CHO/DHFR cells by using FREE-STYLE™ MAX Reagent (Invitrogen). 48 hours post-transfection, the cells were initially passaged and screened with Opti CHO medium supplemented with 500 μg/ml G418 until the cell viability restored to above 85%. A second round screening was performed in a screening medium containing 500 nM MTX. Single clone was selected with ClonePix FL. After 7-10 days of monoclonal culture, the expression level of HP6H8-1 in the culture supernatant was 2.23±0.18 g/L as measured with HTRF method (shown in FIG. 6).

Example 11: Determination of the Specificity of Humanized Anti-hBASIGIN Antibody Immunohistochemical method was used to detect the specific binding of antibody HP6H8-1 to tumor tissue, and the immunohistochemical cross-reactivity of the antibody was investigated. 3% $H_2O_2$ was used to block and inactivate endogenous peroxidase, normal sheep serum working solution was used for blocking, HP6H8-1 was used as primary antibody, biotin-labeled rabbit anti-human Fc antibody was used as secondary antibody, horseradish peroxidase-labeled streptomycin albumin solution was used as label reagent, DAB was used for colorization, and hematoxylin was used for re-stain. After the sample were dehydrated, the slides carrying it were mounted for microscopic examination.

Figure 7:
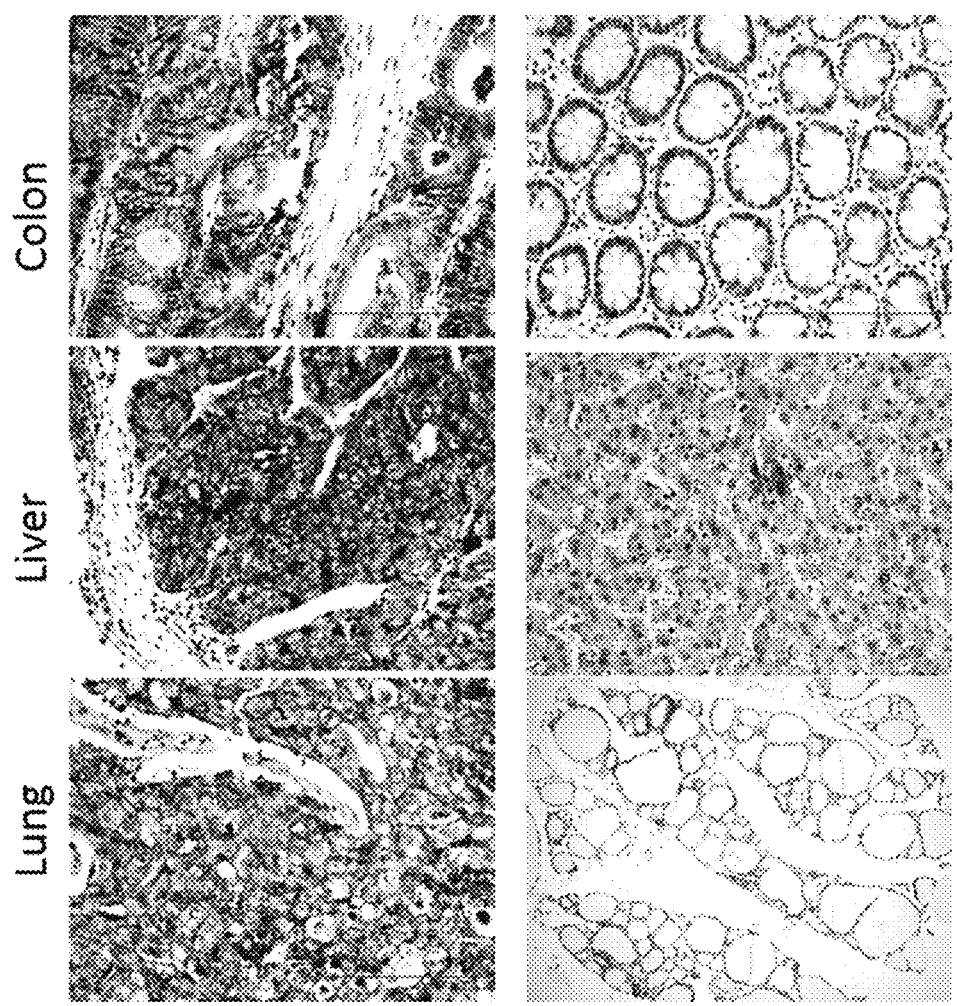
FIG. 7 shows the immunohistochemical staining results of HP6H8-1 in malignant tissues of colon, liver and lung cancers.

Results were shown in FIG. 7, specific colorization of the antibody HP6H8-1 was observed in lung cancer, liver cancer, colon cancer and other malignant tumor tissues, but rarely in normal tissues, different degrees of colorization were marked as "++" or "+++".

The above results shows that the humanized antibody generated in present disclosure basing on the CDR grafting can specifically recognize human BASIGIN.

Example 12: In Vitro Antimalarial Test with HP6H8-1 Antibody

Human erythrocytes (0-type) were infected with *Plasmodium falciparum* strains Dd2, 3D7, FCC1 and Nf54, respectively. When the infection rate was 21% and the malarial roset was ≥80%, the antimalarial test was performed. The culture was diluted with monoclonal antibody to set the initial level of parasitemia to 0.5%, fresh erythrocytes were added to set an initial hematocrit to 2%, the monoclonal antibody HP6H8-1 was added at a concentrations of 100, 10, 1, 0.1, 0.01 μg/ml, respectively, each concentration gradient was tested in triplicate. After cultured for 72 hrs at 37° C., thin blood smear was prepared and observed under 100× oil microscope to count the parasite rate. The experiment was independently repeated for three times, the results were averaged, and analyzed with SPSS for statistics.

Figure 8:
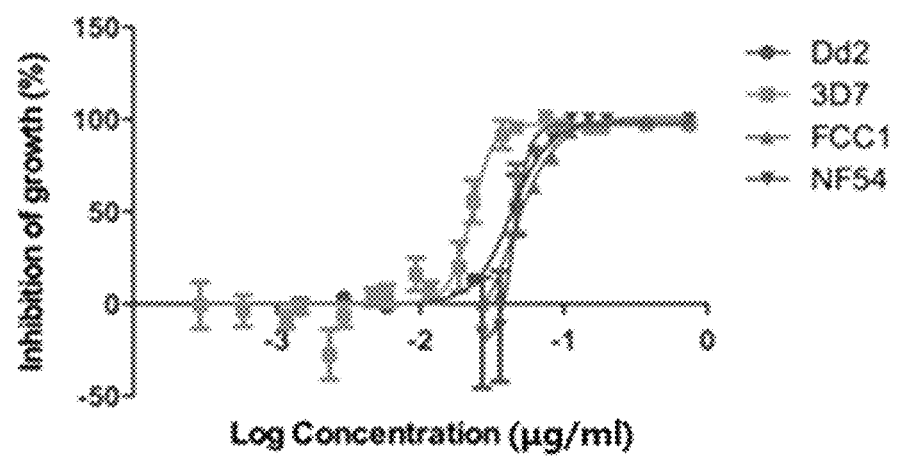
FIG. 8 presents the in vitro inhibition results of *Plasmodium falciparum* invasion of erythrocyte by humanized antibody HP6H8-1, wherein result data is shown as mean±S.E.M.

The in vitro pharmacodynamics results of humanized HP6-18-1 monoclonal antibody against *Plasmodium falciparum* strains Dd2, 3D7, FCC1 and Nf54 were shown in FIG. 8. After 72 hrs post administration of the antibody, humanized monoclonal antibody HP6H8-1 showed significant antimalarial effect to all *Plasmodium falciparum* strains, and IC50 were 0.04, 0.02, 0.04, and 0.05 mg/ml respectively.

What is claimed for is:

1. A humanized monoclonal anti-BASIGIN antibody or antigen binding fragment thereof, which comprises a heavy chain variable region ($V_H$) comprising three heavy chain CDRs, wherein HCDR1 comprises the amino acid sequence of SEQ ID NO: 9, HCDR2 comprises the amino acid sequence of SEQ ID NO: 10, and HCDR3 comprises the amino acid sequence of SEQ ID NO: 11, and a light chain variable region ($V_L$) comprising three CDRs, wherein LCDR1 comprises the amino acid sequence of SEQ ID NO: 22, LCDR2 comprises the amino acid sequence of SEQ ID NO: 23, and LCDR3 comprises the amino acid sequence of SEQ ID NO: 24; and wherein the $V_H$ comprises: the amino acid sequence of SEQ ID NO: 1 (EVQLXESGGGLVQPGGSLRLSCX-ASGFTFSNFWMNWVRQAPGKGLEWVXEIRLKS NNYATHYAESVKGRFTISRDDSKXX-LYLQMNSLXTEDTXVYYCTSYDYEYWGQGT LVTVSA), wherein the X at position i of SEQ ID NO: 1 is referred to as $X_{Hi}$ (i=5, 23, 49, 79, 80, 89 or 94), and wherein $X_{H5}$ is V, $X_{H23}$ is A, $X_{H49}$ is S or A, $X_{H79}$ is N, $X_{H80}$ is T, $X_{H89}$ is K or R, and $X_{H94}$ is A; and wherein the $V_L$ comprises the amino acid sequence of SEQ ID NO: 2 (DIQMTQSPXXLSXSVGDRVTXXCKA-SENVGTYVSWYQQKPGXXPKLLIYGASNRY TGVPXRFTGXGSGTDFTLTISSLQXXDX-ATYYCGQSYSYPFTFGSGTKLEIK), wherein the X at position j of SEQ ID NO: 2 is referred to as $X_{Lj}$ (j=9, 10, 13, 21, 22, 42, 43, 60, 65, 80, 81 or 83), and wherein $X_{L9}$ is S or A, $X_{L10}$ is T or S, $X_{L13}$ is A, $X_{L21}$ is L or I, $X_{L22}$ is S or T, $X_{L42}$ is K or Q, $X_{L43}$ is A or T, $X_{L60}$ is S, $X_{L65}$ is S or T, $X_{L80}$ is P, $X_{L181}$ is E or D, and $X_{L83}$ is F.

2. The humanized monoclonal anti-BASIGIN antibody or antigen binding fragment thereof of claim 1, wherein the $V_H$ comprises the amino acid sequence of SEQ ID NO:3, SEQ ID NO:5 or SEQ ID NO:7.

3. The humanized monoclonal anti-BASIGIN antibody or antigen binding fragment thereof of claim 1, wherein the $V_L$ comprises the amino acid sequence of SEQ ID NO:16, SEQ ID NO:18 or SEQ ID NO:20.

4. The humanized monoclonal anti-BASIGIN antibody or antigen binding fragment thereof of claim 1, wherein the humanized anti-BASIGIN antibody or antigen binding fragment thereof binds to BASIGIN with a $K_D$ between $5\times10^{-11}$ M and $1.1\times10^{-10}$ M.

5. An isolated nucleic acid sequence encoding the humanized monoclonal anti-BASIGIN antibody or antigen binding fragment thereof of claim 1, wherein the isolated nucleic acid sequence is free of other nucleic acid molecules.

6. The isolated nucleic acid sequence of claim 5, which comprises the nucleotide sequence of SEQ ID NO:4, SEQ ID NO:6, SEQ ID NO:8, SEQ ID NO:17, SEQ ID NO:19, or SEQ ID NO:21.

7. The isolated nucleic acid sequence of claim 5, which further comprises a nucleotide sequence encoding a constant region of human IgG heavy chain or human kappa chain.

8. A composition comprising (a) the humanized monoclonal anti-BASIGIN antibody or antigen binding fragment thereof of claim 1, and (b) a pharmaceutically acceptable carrier.

9. A method for therapeutic treatment of a BASIGIN related disease in a subject, wherein the method comprises administering an effective amount of the composition of claim 8 to the subject, wherein the subject is human, and wherein the BASIGIN related disease is basigin-expressing cancer or malaria, and wherein the subject has either the basigin-expressing cancer or malaria.

10. The method of claim 9, wherein the cancer is lung cancer, liver cancer, cervical cancer, colon cancer, breast cancer, ovarian cancer, esophageal cancer or gastric cancer.

11. A humanized monoclonal anti-BASIGIN antibody or antigen binding fragment thereof, which comprises a heavy chain variable region ($V_H$) comprising the amino acid sequence of SEQ ID NO: 5, and a light chain variable region ($V_L$) comprising the amino acid sequence of SEQ ID NO: 18.

12. A humanized monoclonal anti-BASIGIN antibody or antigen binding fragment thereof, which comprises a heavy chain variable region ($V_H$) comprising the amino acid sequence of SEQ ID NO: 7, and a light chain variable region ($V_L$) comprising the amino acid sequence of SEQ ID NO: 20.

* * * * *